US008916516B2

(12) United States Patent
Dobson

(10) Patent No.: US 8,916,516 B2
(45) **Date of Patent: *Dec. 23, 2014**

(54) TREATMENT OF FUNGAL AND/OR PROTIST INFECTIONS

(75) Inventor: Curtis Dobson, Manchester (GB)

(73) Assignee: AI2 Limited, Manchester (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/335,549

(22) Filed: Dec. 22, 2011

(65) Prior Publication Data

US 2012/0258907 A1 Oct. 11, 2012

Related U.S. Application Data

(63) Continuation of application No. 11/916,627, filed as application No. PCT/GB2006/002350 on Jun. 26, 2006, now abandoned.

(30) Foreign Application Priority Data

Jun. 28, 2005 (GB) ..................................... 0513096

(51) Int. Cl.
*A61K 38/00* (2006.01)
*A01N 37/18* (2006.01)
*A61K 38/10* (2006.01)
*C07K 14/775* (2006.01)

(52) U.S. Cl.
CPC ............... *C07K 14/775* (2013.01); *A61K 38/10* (2013.01)
USPC ............... 514/1.1; 514/1.4; 514/2.3; 514/2.4; 514/3.3

(58) Field of Classification Search
None
See application file for complete search history.

(56) References Cited

U.S. PATENT DOCUMENTS

| | | | | |
|---|---|---|---|---|
| 7,691,382 | B2 | 4/2010 | Dobson | |
| 8,017,579 | B2 | 9/2011 | Dobson | |
| 8,524,861 | B2 | 9/2013 | Dobson et al. | |
| 2002/0164789 | A1 | 11/2002 | Laskowitz et al. | |
| 2005/0058689 | A1* | 3/2005 | McDaniel | 424/426 |
| 2005/0208078 | A1 | 9/2005 | Hoffman et al. | |
| 2005/0260581 | A1 | 11/2005 | Fontana et al. | |
| 2005/0266017 | A1 | 12/2005 | Druilhe et al. | |
| 2007/0117746 | A1 | 5/2007 | Dobson | |
| 2008/0207508 | A1 | 8/2008 | Dobson | |
| 2009/0048171 | A1 | 2/2009 | Dobson | |
| 2009/0169598 | A1 | 7/2009 | Crutcher | |
| 2010/0221273 | A1 | 9/2010 | Dobson | |
| 2013/0150288 | A1 | 6/2013 | Dobson | |

FOREIGN PATENT DOCUMENTS

| | | | |
|---|---|---|---|
| WO | 9201462 | A1 | 2/1992 |
| WO | 9404177 | A1 | 3/1994 |
| WO | 9842751 | A1 | 10/1998 |
| WO | 9937664 | A1 | 7/1999 |
| WO | 9945950 | A2 | 9/1999 |
| WO | 0215923 | A1 | 2/2002 |
| WO | 03/026479 | A2 | 4/2003 |
| WO | 03052076 | A2 | 6/2003 |
| WO | 2005039534 | A1 | 5/2005 |
| WO | 2005058959 | A2 | 6/2005 |
| WO | 2005061359 | A2 | 7/2005 |
| WO | 2005082399 | A2 | 9/2005 |
| WO | 2007000584 | A1 | 1/2007 |

OTHER PUBLICATIONS

Clay et al. Localization of a domain in Apoliopoprotein E with both cytostatic and cytotoxic activity. Biochemistry. (1995): 34:11142-11151.
Gait et al. Progress in anti-HIV structure-based drug design. TIBTECH. (1995). 13.430-438.
Hirsch el al. Antiretroviral drug resistance testing in adults with HIV infection: Implications for clinical management. JAMA. (1998). 279(24)1984-1991.
Owens et al. Apolipoprotein A-I and its amphipathic helix peptide analogues inhibit human immunodeficiency virus-induced syncytium formation. J. Clin. Invest. (1990). 86:1142-1150.
Srinivas et al. Inhibition of virus-induced cell fusion by Apolipoprotein A-I and its amphipathic peptide analogs. J. Cellular Biochemistry. (1991). 45:224-237.
U.S. Appl. No. 10/580,761 Office Action dated Jan. 9, 2008.
U.S. Appl. No. 10/580,761 Office Action dated Jun. 24, 2008.
U.S. Appl. No. 10/580,761 Office Action dated Nov. 26, 2008..
U.S. Appl. No. 10/580,761 Office Action dated Jun. 9, 2009.
U.S. Appl. No. 10/580,761 Notice of Allowance dated Nov. 2, 2009.
U.S. Appl. No. 10/580,984 Office Action dated Jun. 25, 2009.
U.S. Appl. No. 10/580;984 Office Action dated Dec. 22, 2009.
U.S. Appl. No. 10/580,984 Office Action dated Jun. 30, 2010.
U.S. Appl. No. 10/580,984 Office Action dated Dec. 3, 2010.
U.S. Appl. No. 10/586,416 Office Action dated Dec. 13, 2010.
PCT/GB04/05360 ISR dated Oct. 4, 2005.
PCT/GB04/05360 Written Opinion dated Oct. 4, 2005.
PCT/GB04/05360 IPRP dated Jun. 20, 2006.
PCT/GB04/05438 ISR dates Oct. 4, 2005.
PCT/GB04/05438 Written Opinion dated Oct. 4, 2005.
PCT/GB04/05438 IPRP dated Jun. 26, 2006.
PCT/GB06/02350 ISR dated Dec. 1, 2006.
PCT/GB06/02350 Written Opinion dated Dec. 1, 2006.
PCT/GB06/02350 IPRP dated Jan. 9, 2008.
PCT/GB05/00769 ISR dated Oct. 18, 2005.
PCT/GB05/00769 Written Opinion dated Oct. 18, 2005.
PCT/GB05/00769 IPRP dated Aug. 30, 2006.
U.S. Appl. No. 10/586,416 Office Action dated May 12, 2011.
U.S. Appl. No. 11/916,627 Restriction Requirement dated Dec. 24, 2009.
U.S. Appl. No. 11/916,627 Office Action dated May 10, 2010.
U.S. Appl. No. 11/916,627 Office Action dated Dec. 15, 2010.
U.S. Appl. No. 11/916,627 Office Action dated Sep. 27, 2011.
Azuma et al. A Synthetic Peptide of Human Apoprotein E with Antibacterial Activity. Peptides. (2000). 21:327-330.
Boman et al. Antibacterial Peptides: Basic Facts and Emerging Concepts. Journal of Internal Medicine. (2003). 254:197-215.
Bradshaw, J.P. Cationic Antimicrobial Peptides, Issues for Potential Clinical Use. Biodrugs (2003). 17(4):223-240.
Law et al. A Cross-Species Comparison of the Apolipoprotein B Domain that Binds to the LDL Receptor. Journal of Lipid Research. (1990) 31:1109-1120

(Continued)

*Primary Examiner* — Albert Navarro

(74) *Attorney, Agent, or Firm* — Linda B. Huber; Nixon Peabody LLP

(57) ABSTRACT

The present invention relates to the use of a polypeptides, comprising repeats of a peptide derived from a Heparan Sulphate Proteoglycan (HSPG) receptor binding region of an apolipoprotein, for treating or preventing a fungal and/or protist infection. The invention further relates to the use of such peptides for treating or preventing the contamination of surfaces or objects with such peptides.

18 Claims, 5 Drawing Sheets

(56) References Cited

OTHER PUBLICATIONS

Raffai et al. Molecular Characterization of Two Monoclonal Antibodies Specific for the LDL Receptor-Binding Site of Human Apolipoprotein E. Journal of Lipid Research (1995). 36: 1905-1918.
Olsson et al. Possible Functional Interactions of Apolipoprotein B-100 Segments that Associate with Cell Proteogylcans and the ApoB/E Receiptor. Arterioseler. Thrornb. Vasc. Biol. (1997). 17:149-155.
Wang et al. Apolipoprotein E (ApoE) Peptide Regulates Tau Phosphorylation via Two Different Signalling Pathways. J. Neurosci. Res. (1998). 51:658-665.
U.S. Appl. No. 10/586,416 Non-Final Office Action dated Jun. 11, 2012.
U.S. Appl. No. 12/702,919 Restriction Requirement dated Dec. 14, 2011.
U.S. Appl. No. 12/702,919 Non-Final Office Action dated Mar. 21, 2012.
U.S. Appl. No. 10/580,984 Notice of Allowance dated Jun. 2, 2011.
U.S. Appl. No. 10/586,416 Final Office Action dated Dec. 19, 2012.
Hamy et al. An Inhibitor of the TatTAR RNA Interaction that effectively suppresses HIV-1 Replication Proc. Natl. Acad. Sci (1997). 94(8):3548-3553.
Motizuki et al. Lipid-binding antimicrobial properties of synthetic peptides of bovine apolipoprotein A-II. Biochemical Journal. (1999). 342(1): 215-221.
Moerman et al. Antibacterial and antifungal properties of x-helical, cationic peptides in the venom of scorpions from southern Africa. Eur. J. Biochem. (2002). 269:4799-4810.
Muller et al. Antimicrobial peptides as potential new antifungals. Mycoses (1999) 42:Suppl 2: 77-82. Abstract.
Vogel et al. Towards a structure-function analysis of bovine lactoferricin and related tryptophan- and arginine-containing peptides. Biochem, Cell. Bio. (2002). 80(1):49-63. Abstract.

* cited by examiner

Figure: 2

Figure 3
a)
Untreated GIN1p
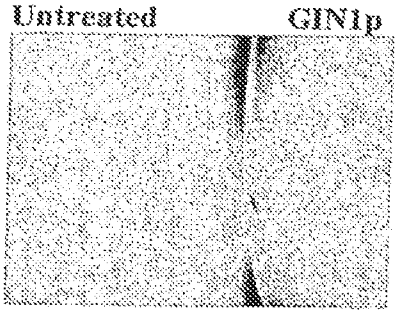
NORMAL ILLUMINATION
Untreated GIN1p
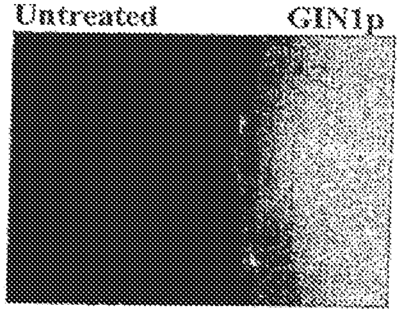
FLUORESCENCE
(b)
GIN1p
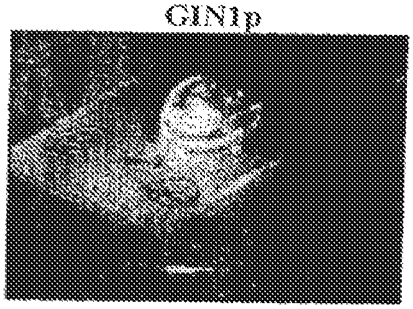
FLUORESCENCE Figure 5
(A)
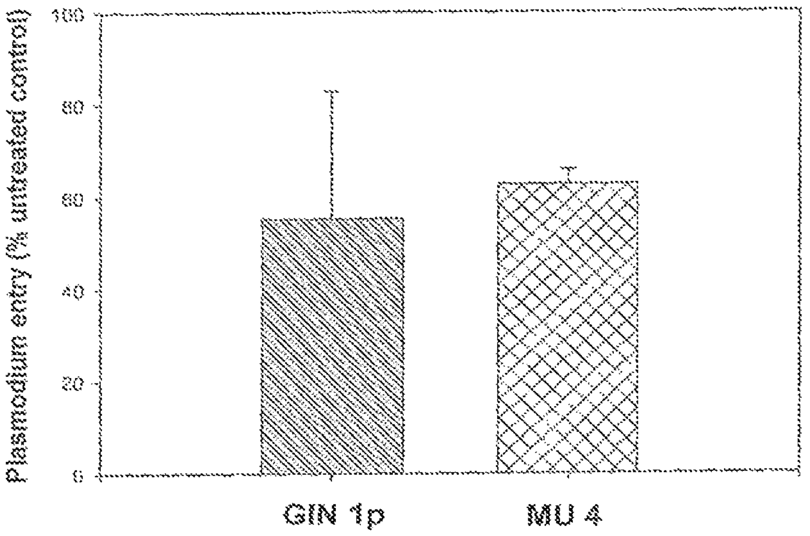
(B)
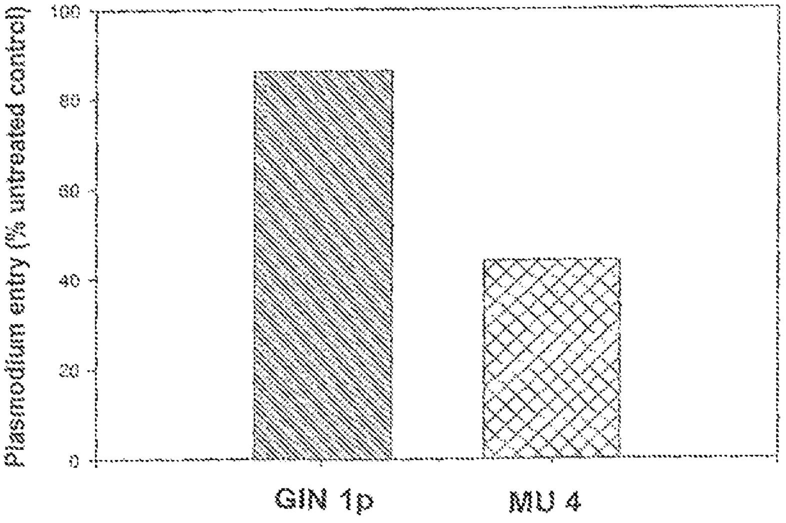

SEQUENCE LISTING

<160> NUMBER OF SEQ ID NOS: 90

<210> SEQ ID NO 1
<211> LENGTH: 37
<212> TYPE: PRT
<213> ORGANISM: Homo sapiens

<400> SEQUENCE: 1

```
Leu Leu Gly Asp Phe Phe Arg Lys Ser Lys Glu Lys Ile Gly Lys Glu
1               5                   10                  15
```

```
Phe Lys Arg Ile Val Gln Arg Ile Lys Asp Phe Leu Arg Asn Leu Val
            20                  25                  30

Pro Arg Thr Glu Ser
        35


<210> SEQ ID NO 2
<211> LENGTH: 30
<212> TYPE: PRT
<213> ORGANISM: Homo sapiens

<400> SEQUENCE: 2

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30


<210> SEQ ID NO 3
<211> LENGTH: 39
<212> TYPE: PRT
<213> ORGANISM: Sus sp.

<400> SEQUENCE: 3

Arg Arg Arg Pro Arg Pro Pro Tyr Leu Pro Arg Pro Arg Pro Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro
        35


<210> SEQ ID NO 4
<211> LENGTH: 13
<212> TYPE: PRT
<213> ORGANISM: Bos sp.

<400> SEQUENCE: 4

Ile Leu Pro Trp Lys Trp Pro Trp Trp Pro Trp Arg Arg
1               5                   10


<210> SEQ ID NO 5
<211> LENGTH: 9
<212> TYPE: PRT
<213> ORGANISM: Homo sapiens

<400> SEQUENCE: 5

Leu Arg Lys Leu Arg Lys Arg Leu Leu
1               5


<210> SEQ ID NO 6
<211> LENGTH: 9
<212> TYPE: PRT
<213> ORGANISM: Homo sapiens

<400> SEQUENCE: 6

Arg Leu Thr Arg Lys Arg Gly Leu Lys
1               5


<210> SEQ ID NO 7
<211> LENGTH: 9
<212> TYPE: PRT
<213> ORGANISM: Artificial
<220> FEATURE:
<223> OTHER INFORMATION: Artificial sequence based on residues of human
      apoB
```

-continued

<400> SEQUENCE: 7

Leu Arg Thr Arg Lys Arg Gly Arg Lys
1 5

<210> SEQ ID NO 8
<211> LENGTH: 18
<212> TYPE: PRT
<213> ORGANISM: Artificial
<220> FEATURE:
<223> OTHER INFORMATION: Tandem repeat of Sequence ID No. 5

<400> SEQUENCE: 8

Leu Arg Lys Leu Arg Lys Arg Leu Leu Leu Arg Lys Leu Arg Lys Arg
1 5 10 15

Leu Leu

<210> SEQ ID NO 9
<211> LENGTH: 18
<212> TYPE: PRT
<213> ORGANISM: Artificial
<220> FEATURE:
<223> OTHER INFORMATION: Artficial polypeptide designated GIN 7 or MU 4

<400> SEQUENCE: 9

Trp Arg Lys Trp Arg Lys Arg Trp Trp Trp Arg Lys Trp Arg Lys Arg
1 5 10 15

Trp Trp

<210> SEQ ID NO 10
<211> LENGTH: 14
<212> TYPE: PRT
<213> ORGANISM: Artificial
<220> FEATURE:
<223> OTHER INFORMATION: Artificial polypeptide designated GIN 32

<400> SEQUENCE: 10

Trp Arg Lys Trp Arg Lys Arg Trp Arg Lys Trp Arg Lys Arg
1 5 10

<210> SEQ ID NO 11
<211> LENGTH: 18
<212> TYPE: PRT
<213> ORGANISM: Artificial
<220> FEATURE:
<223> OTHER INFORMATION: Artificial polypeptide designated GIN 34

<400> SEQUENCE: 11

Trp Arg Lys Trp Arg Lys Arg Trp Trp Leu Arg Lys Leu Arg Lys Arg
1 5 10 15

Leu Leu

<210> SEQ ID NO 12
<211> LENGTH: 18
<212> TYPE: PRT
<213> ORGANISM: Artificial
<220> FEATURE:
<223> OTHER INFORMATION: Artificial polypeptide designated GIN 41 or MU6

<400> SEQUENCE: 12

Tyr Arg Lys Tyr Arg Lys Arg Tyr Tyr Tyr Arg Lys Tyr Arg Lys Arg
1 5 10 15

Tyr Tyr

<210> SEQ ID NO 13
<211> LENGTH: 14
<212> TYPE: PRT
<213> ORGANISM: Artificial
<220> FEATURE:
<223> OTHER INFORMATION: Artficial polypeptide designated GIN 8

<400> SEQUENCE: 13

Leu Arg Lys Leu Arg Lys Arg Leu Arg Lys Leu Arg Lys Arg
1 5 10

<210> SEQ ID NO 14
<211> LENGTH: 15
<212> TYPE: PRT
<213> ORGANISM: Artificial
<220> FEATURE:
<223> OTHER INFORMATION: Artificial polypeptide designated GIN 2

<400> SEQUENCE: 14

Leu Arg Lys Arg Leu Leu Leu Arg Lys Leu Arg Lys Arg Leu Leu
1 5 10 15

<210> SEQ ID NO 15
<211> LENGTH: 18
<212> TYPE: PRT
<213> ORGANISM: Artificial
<220> FEATURE:
<223> OTHER INFORMATION: Artficial polypeptide designated MU7

<400> SEQUENCE: 15

Phe Arg Lys Phe Arg Lys Arg Phe Phe Phe Arg Lys Phe Arg Lys Arg
1 5 10 15

Phe Phe

<210> SEQ ID NO 16
<211> LENGTH: 17
<212> TYPE: PRT
<213> ORGANISM: Artificial
<220> FEATURE:
<223> OTHER INFORMATION: Artificial polypeptide designated MU 58

<400> SEQUENCE: 16

Trp Arg Lys Trp Arg Lys Arg Trp Trp Arg Lys Trp Arg Lys Arg Trp
1 5 10 15

Trp

<210> SEQ ID NO 17
<211> LENGTH: 15
<212> TYPE: PRT
<213> ORGANISM: Artificial
<220> FEATURE:
<223> OTHER INFORMATION: Artificial polypeptide designated MU59

<400> SEQUENCE: 17

Trp Arg Lys Trp Arg Lys Arg Trp Arg Lys Trp Arg Lys Arg Trp
1 5 10 15

<210> SEQ ID NO 18
<211> LENGTH: 18
<212> TYPE: PRT
<213> ORGANISM: Artificial
<220> FEATURE:
<223> OTHER INFORMATION: Artificial polypeptide designated MU 60

<400> SEQUENCE: 18

-continued

```
Trp Arg Lys Trp Arg Lys Arg Trp Trp Phe Arg Lys Trp Arg Lys Arg
1               5                   10                  15

Trp Trp


<210> SEQ ID NO 19
<211> LENGTH: 18
<212> TYPE: PRT
<213> ORGANISM: Artificial
<220> FEATURE:
<223> OTHER INFORMATION: Artificial polypeptide designated MU 61

<400> SEQUENCE: 19

Trp Arg Lys Trp Arg Lys Arg Phe Phe Trp Arg Lys Trp Arg Lys Arg
1               5                   10                  15

Phe Phe


<210> SEQ ID NO 20
<211> LENGTH: 14
<212> TYPE: PRT
<213> ORGANISM: Artificial
<220> FEATURE:
<223> OTHER INFORMATION: Artificial polypeptide designated MU 81

<400> SEQUENCE: 20

Trp Arg Lys Arg Trp Trp Arg Trp Arg Lys Arg Trp Trp Arg
1               5                   10


<210> SEQ ID NO 21
<211> LENGTH: 20
<212> TYPE: PRT
<213> ORGANISM: Artificial
<220> FEATURE:
<223> OTHER INFORMATION: Artificial polypeptide designated MU 82

<400> SEQUENCE: 21

Leu Arg Lys Leu Arg Lys Arg Leu Leu Arg Leu Arg Lys Leu Arg Lys
1               5                   10                  15

Arg Leu Leu Arg
            20


<210> SEQ ID NO 22
<211> LENGTH: 20
<212> TYPE: PRT
<213> ORGANISM: Artificial
<220> FEATURE:
<223> OTHER INFORMATION: Artficial polypeptide designated MU 83

<400> SEQUENCE: 22

Trp Arg Lys Trp Arg Lys Arg Trp Trp Arg Trp Arg Lys Trp Arg Lys
1               5                   10                  15

Arg Trp Trp Arg
            20


<210> SEQ ID NO 23
<211> LENGTH: 18
<212> TYPE: PRT
<213> ORGANISM: Artificial
<220> FEATURE:
<223> OTHER INFORMATION: Artificial polypeptide designated MU 111

<400> SEQUENCE: 23

Leu Arg Lys Leu Arg Lys Arg Leu Leu Trp Arg Lys Trp Arg Lys Arg
1               5                   10                  15

Trp Trp
```

<210> SEQ ID NO 24
<211> LENGTH: 18
<212> TYPE: PRT
<213> ORGANISM: Artificial
<220> FEATURE:
<223> OTHER INFORMATION: Artificial polypeptide designated MU 112

<400> SEQUENCE: 24

Leu Arg Lys Leu Arg Lys Arg Leu Leu Leu Arg Lys Leu Arg Lys Arg
1 5 10 15

Trp Trp

<210> SEQ ID NO 25
<211> LENGTH: 18
<212> TYPE: PRT
<213> ORGANISM: Artificial
<220> FEATURE:
<223> OTHER INFORMATION: Artificial polypeptide designated MU 113

<400> SEQUENCE: 25

Leu Arg Lys Leu Arg Lys Arg Leu Leu Trp Arg Lys Trp Arg Lys Arg
1 5 10 15

Leu Leu

<210> SEQ ID NO 26
<211> LENGTH: 18
<212> TYPE: PRT
<213> ORGANISM: Artificial
<220> FEATURE:
<223> OTHER INFORMATION: Artificial polypeptide designated MU 114

<400> SEQUENCE: 26

Trp Arg Lys Trp Arg Lys Arg Leu Leu Leu Arg Lys Leu Arg Lys Arg
1 5 10 15

Leu Leu

<210> SEQ ID NO 27
<211> LENGTH: 18
<212> TYPE: PRT
<213> ORGANISM: Artificial
<220> FEATURE:
<223> OTHER INFORMATION: Artificial polypeptide designated MU 115

<400> SEQUENCE: 27

Trp Arg Lys Leu Arg Lys Arg Leu Leu Leu Arg Lys Leu Arg Lys Arg
1 5 10 15

Leu Leu

<210> SEQ ID NO 28
<211> LENGTH: 17
<212> TYPE: PRT
<213> ORGANISM: Artificial
<220> FEATURE:
<223> OTHER INFORMATION: Artificial polypeptide designated MU 116

<400> SEQUENCE: 28

Trp Arg Lys Trp Arg Lys Phe Phe Phe Arg Lys Trp Arg Lys Arg Trp
1 5 10 15

Trp

<210> SEQ ID NO 29
<211> LENGTH: 18

<212> TYPE: PRT
<213> ORGANISM: Artificial
<220> FEATURE:
<223> OTHER INFORMATION: Artificial polypeptide designated MU 117

<400> SEQUENCE: 29

Trp Arg Lys Trp Arg Lys Arg Trp Trp Phe Arg Lys Phe Arg Lys Arg
1 5 10 15

Phe Phe

<210> SEQ ID NO 30
<211> LENGTH: 18
<212> TYPE: PRT
<213> ORGANISM: Artificial
<220> FEATURE:
<223> OTHER INFORMATION: Artficial polypeptide designated MU 12

<400> SEQUENCE: 30

Cys Arg Lys Cys Arg Lys Arg Cys Cys Cys Arg Lys Cys Arg Lys Arg
1 5 10 15

Cys Cys

<210> SEQ ID NO 31
<211> LENGTH: 18
<212> TYPE: PRT
<213> ORGANISM: Artificial
<220> FEATURE:
<223> OTHER INFORMATION: Artificial polypeptide designated MU 16

<400> SEQUENCE: 31

Arg Arg Lys Arg Arg Lys Arg Arg Arg Arg Arg Lys Arg Arg Lys Arg
1 5 10 15

Arg Arg

<210> SEQ ID NO 32
<211> LENGTH: 18
<212> TYPE: PRT
<213> ORGANISM: Artificial
<220> FEATURE:
<223> OTHER INFORMATION: Artificial polypeptide designated MU 16

<400> SEQUENCE: 32

Met Arg Lys Met Arg Lys Arg Met Met Met Arg Lys Met Arg Lys Arg
1 5 10 15

Met Met

<210> SEQ ID NO 33
<211> LENGTH: 18
<212> TYPE: PRT
<213> ORGANISM: Artificial
<220> FEATURE:
<223> OTHER INFORMATION: Artficial polypeptide designated MU 8

<400> SEQUENCE: 33

Ile Arg Lys Ile Arg Lys Arg Ile Ile Ile Arg Lys Ile Arg Lys Arg
1 5 10 15

Ile Ile

<210> SEQ ID NO 34
<211> LENGTH: 18
<212> TYPE: PRT
<213> ORGANISM: Artificial
<220> FEATURE:
<223> OTHER INFORMATION: Artificial polypeptide designated MU 19

<400> SEQUENCE: 34

His Arg Lys His Arg Lys Arg His His His Arg Lys His Arg Lys Arg
1 5 10 15

His His

<210> SEQ ID NO 35
<211> LENGTH: 22
<212> TYPE: PRT
<213> ORGANISM: Artificial
<220> FEATURE:
<223> OTHER INFORMATION: Artificial polypeptide designated GIN 11

<400> SEQUENCE: 35

Gln Ser Thr Glu Glu Leu Arg Val Arg Leu Ala Ser His Leu Arg Lys
1 5 10 15

Leu Arg Lys Arg Leu Leu
20

<210> SEQ ID NO 36
<211> LENGTH: 18
<212> TYPE: PRT
<213> ORGANISM: Artificial
<220> FEATURE:
<223> OTHER INFORMATION: Artificial 18-mer based on Sequence ID No. 6

<400> SEQUENCE: 36

Arg Leu Thr Arg Lys Arg Gly Leu Lys Arg Leu Thr Arg Lys Arg Gly
1 5 10 15

Leu Lys

<210> SEQ ID NO 37
<211> LENGTH: 14
<212> TYPE: PRT
<213> ORGANISM: Artificial
<220> FEATURE:
<223> OTHER INFORMATION: Artificial polypeptide designated GIN 36

<400> SEQUENCE: 37

Arg Thr Arg Lys Arg Gly Arg Arg Thr Arg Lys Arg Gly Arg
1 5 10

<210> SEQ ID NO 38
<211> LENGTH: 14
<212> TYPE: PRT
<213> ORGANISM: Artificial
<220> FEATURE:
<223> OTHER INFORMATION: Artificial polypeptide designated GIN 37

<400> SEQUENCE: 38

Leu Arg Lys Arg Lys Arg Leu Leu Arg Lys Arg Lys Arg Leu
1 5 10

<210> SEQ ID NO 39
<211> LENGTH: 18
<212> TYPE: PRT
<213> ORGANISM: Artificial
<220> FEATURE:
<223> OTHER INFORMATION: Artificial polypeptide designated GIN 38

<400> SEQUENCE: 39

Leu Arg Lys Arg Lys Arg Leu Arg Lys Leu Arg Lys Arg Lys Arg Leu
1 5 10 15

Arg Lys

<210> SEQ ID NO 40
<211> LENGTH: 18
<212> TYPE: PRT
<213> ORGANISM: Artificial
<220> FEATURE:
<223> OTHER INFORMATION: Artificial polypeptide designated GIN 33

<400> SEQUENCE: 40

Trp Arg Trp Arg Lys Arg Trp Arg Lys Trp Arg Trp Arg Lys Arg Trp
1 5 10 15

Arg Lys

<210> SEQ ID NO 41
<211> LENGTH: 18
<212> TYPE: PRT
<213> ORGANISM: Artificial
<220> FEATURE:
<223> OTHER INFORMATION: Artificial polypeptide designated MU 24

<400> SEQUENCE: 41

Leu Leu Arg Lys Arg Leu Lys Arg Leu Leu Leu Arg Lys Arg Leu Lys
1 5 10 15

Arg Leu

<210> SEQ ID NO 42
<211> LENGTH: 18
<212> TYPE: PRT
<213> ORGANISM: Artificial
<220> FEATURE:
<223> OTHER INFORMATION: Artificial polypeptide designated MU 28

<400> SEQUENCE: 42

Arg Arg Trp Arg Lys Arg Trp Arg Lys Trp Arg Trp Arg Lys Arg Trp
1 5 10 15

Arg Lys

<210> SEQ ID NO 43
<211> LENGTH: 18
<212> TYPE: PRT
<213> ORGANISM: Artificial
<220> FEATURE:
<223> OTHER INFORMATION: Artificial polypeptide designated MU 29

<400> SEQUENCE: 43

Lys Arg Trp Arg Lys Arg Trp Arg Lys Trp Arg Trp Arg Lys Arg Trp
1 5 10 15

Arg Lys

<210> SEQ ID NO 44
<211> LENGTH: 18
<212> TYPE: PRT
<213> ORGANISM: Artificial
<220> FEATURE:
<223> OTHER INFORMATION: Artificial polypeptide designated MU 30

<400> SEQUENCE: 44

Leu Arg Trp Arg Lys Arg Trp Arg Lys Trp Arg Trp Arg Lys Arg Trp
1 5 10 15

Arg Lys

<210> SEQ ID NO 45
<211> LENGTH: 18

<212> TYPE: PRT
<213> ORGANISM: Artificial
<220> FEATURE:
<223> OTHER INFORMATION: Artificial polypeptide designated MU 31

<400> SEQUENCE: 45

His Arg Trp Arg Lys Arg Trp Arg Lys Trp Arg Trp Arg Lys Arg Trp
1 5 10 15

Arg Lys

<210> SEQ ID NO 46
<211> LENGTH: 17
<212> TYPE: PRT
<213> ORGANISM: Artificial
<220> FEATURE:
<223> OTHER INFORMATION: Artificial polypeptide designated MU 32

<400> SEQUENCE: 46

Arg Trp Arg Lys Arg Trp Arg Lys Trp Arg Trp Arg Lys Arg Trp Arg
1 5 10 15

Lys

<210> SEQ ID NO 47
<211> LENGTH: 18
<212> TYPE: PRT
<213> ORGANISM: Artificial
<220> FEATURE:
<223> OTHER INFORMATION: Artificial polypeptide designated MU 33

<400> SEQUENCE: 47

Arg Arg Trp Arg Lys Arg Trp Arg Lys Arg Arg Trp Arg Lys Arg Trp
1 5 10 15

Arg Lys

<210> SEQ ID NO 48
<211> LENGTH: 18
<212> TYPE: PRT
<213> ORGANISM: Artificial
<220> FEATURE:
<223> OTHER INFORMATION: Artificial polypeptide designated MU 35

<400> SEQUENCE: 48

Leu Arg Trp Arg Lys Arg Trp Arg Lys Leu Arg Trp Arg Lys Arg Trp
1 5 10 15

Arg Lys

<210> SEQ ID NO 49
<211> LENGTH: 18
<212> TYPE: PRT
<213> ORGANISM: Artificial
<220> FEATURE:
<223> OTHER INFORMATION: Artificial polypeptide designated MU 36

<400> SEQUENCE: 49

His Arg Trp Arg Lys Arg Trp Arg Lys His Arg Trp Arg Lys Arg Trp
1 5 10 15

Arg Lys

<210> SEQ ID NO 50
<211> LENGTH: 16
<212> TYPE: PRT
<213> ORGANISM: Artificial
<220> FEATURE:
<223> OTHER INFORMATION: Artificial polypeptide designated MU 37

<400> SEQUENCE: 50

Arg Trp Arg Lys Arg Trp Arg Lys Arg Trp Arg Lys Arg Trp Arg Lys
1 5 10 15

<210> SEQ ID NO 51
<211> LENGTH: 16
<212> TYPE: PRT
<213> ORGANISM: Artificial
<220> FEATURE:
<223> OTHER INFORMATION: Artificial polypeptide designated MU 69

<400> SEQUENCE: 51

Arg Trp Arg Lys Arg Gly Arg Lys Arg Trp Arg Lys Arg Gly Arg Lys
1 5 10 15

<210> SEQ ID NO 52
<211> LENGTH: 16
<212> TYPE: PRT
<213> ORGANISM: Artificial
<220> FEATURE:
<223> OTHER INFORMATION: Artificial polypeptide designated MU 71

<400> SEQUENCE: 52

Arg Trp Arg Lys Arg Trp Arg Lys Arg Trp Arg Lys Arg Trp Arg Lys
1 5 10 15

<210> SEQ ID NO 53
<211> LENGTH: 14
<212> TYPE: PRT
<213> ORGANISM: Artificial
<220> FEATURE:
<223> OTHER INFORMATION: Artificial polypeptide designated MU 73

<400> SEQUENCE: 53

Arg Lys Arg Gly Trp Lys Trp Arg Lys Arg Gly Trp Lys Trp
1 5 10

<210> SEQ ID NO 54
<211> LENGTH: 14
<212> TYPE: PRT
<213> ORGANISM: Artificial
<220> FEATURE:
<223> OTHER INFORMATION: Artificial polypeptide designated MU 74

<400> SEQUENCE: 54

Arg Leu Thr Arg Lys Arg Gly Arg Leu Thr Arg Lys Arg Gly
1 5 10

<210> SEQ ID NO 55
<211> LENGTH: 18
<212> TYPE: PRT
<213> ORGANISM: Artificial
<220> FEATURE:
<223> OTHER INFORMATION: Artificial polypeptide designated MU 27

<400> SEQUENCE: 55

Trp Arg Trp Arg Lys Arg Trp Arg Lys Trp Arg Trp Arg Lys Arg Trp
1 5 10 15

Arg Lys

<210> SEQ ID NO 56
<211> LENGTH: 27
<212> TYPE: DNA
<213> ORGANISM: Homo sapiens

<400> SEQUENCE: 56
cttcgtaaac ttcgtaaacg tcttctt 27

<210> SEQ ID NO 57
<211> LENGTH: 27
<212> TYPE: DNA
<213> ORGANISM: Homo sapiens

<400> SEQUENCE: 57
cgtcttactc gtaaacgtgg tcttaaa 27

<210> SEQ ID NO 58
<211> LENGTH: 45
<212> TYPE: DNA
<213> ORGANISM: Artificial
<220> FEATURE:
<223> OTHER INFORMATION: Artificial nucleic acid encoding polypeptide of the invention

<400> SEQUENCE: 58
cttcgtaaac gtcttcttct tcgtaaactt cgtaaacgtc ttctt 45

<210> SEQ ID NO 59
<211> LENGTH: 66
<212> TYPE: DNA
<213> ORGANISM: Artificial
<220> FEATURE:
<223> OTHER INFORMATION: Artificial nucleic acid encoding polypeptide of the invention

<400> SEQUENCE: 59
caatctactg aagaacttcg tgttcgtctt gctagtcatc ttcgtaaact tcgtaaacgt 60
cttctt 66

<210> SEQ ID NO 60
<211> LENGTH: 180
<212> TYPE: DNA
<213> ORGANISM: Artificial
<220> FEATURE:
<223> OTHER INFORMATION: Artificial nucleic acid encoding polypeptide of the invention

<400> SEQUENCE: 60
cttcgtgttc gtcttgctag tcatcttcgt aaacttcgta aacgtcttct tcgtgatgct 60
gatgatcttc aaaaacgtct tgctgtttat cttcgtgttc gtcttgctag tcatcttcgt 120
aaacttcgta aacgtcttct tcgtgatgct gatgatcttc aaaaacgtct tgctgtttat 180

<210> SEQ ID NO 61
<211> LENGTH: 54
<212> TYPE: DNA
<213> ORGANISM: Artificial
<220> FEATURE:
<223> OTHER INFORMATION: Artificial nucleic acid encoding polypeptide of the invention

<400> SEQUENCE: 61
cttcgtaaac ttcgtaaacg tcttcttctt cgtaaacttc gtaaacgtct tctt 54

<210> SEQ ID NO 62
<211> LENGTH: 54
<212> TYPE: DNA
<213> ORGANISM: Artificial
<220> FEATURE:
<223> OTHER INFORMATION: Artificial nucleic acid encoding polypeptide of the invention

<400> SEQUENCE: 62
tggcgtaaat ggcgtaaacg ttggtggtgg cgtaaatggc gtaaacgttg gtgg 54

<210> SEQ ID NO 63
<211> LENGTH: 48
<212> TYPE: DNA
<213> ORGANISM: Artificial
<220> FEATURE:
<223> OTHER INFORMATION: Artificial nucleic acid encoding polypeptide of the invention

<400> SEQUENCE: 63
tggcgtaaat ggcgtaaacg ttggtggcgt aaatggcgta aacgttgg 48

<210> SEQ ID NO 64
<211> LENGTH: 54
<212> TYPE: DNA
<213> ORGANISM: Artificial
<220> FEATURE:
<223> OTHER INFORMATION: Artificial nucleic acid encoding polypeptide of the invention

<400> SEQUENCE: 64
tggcgtaaat ggcgtaaacg ttggtggctt cgtaaacttc gtaaacgtct tctt 54

<210> SEQ ID NO 65
<211> LENGTH: 54
<212> TYPE: DNA
<213> ORGANISM: Artificial
<220> FEATURE:
<223> OTHER INFORMATION: Artificial nucleic acid encoding polypeptide of the invention

<400> SEQUENCE: 65
tatcgtaaat atcgtaaacg ttattattat cgtaaatatc gtaaacgtta ttat 54

<210> SEQ ID NO 66
<211> LENGTH: 42
<212> TYPE: DNA
<213> ORGANISM: Artificial
<220> FEATURE:
<223> OTHER INFORMATION: Artificial nucleic acid encoding polypeptide of the invention

<400> SEQUENCE: 66
cttcgtaaac ttcgtaaacg tcttcgtaaa cttcgtaaac gt 42

<210> SEQ ID NO 67
<211> LENGTH: 54
<212> TYPE: DNA
<213> ORGANISM: Artificial
<220> FEATURE:
<223> OTHER INFORMATION: Artificial nucleic acid encoding polypeptide of the invention

<400> SEQUENCE: 67
cgtcttactc gtaaacgtgg tcttaaacgt cttactcgta aacgtggtct taaa 54

<210> SEQ ID NO 68
<211> LENGTH: 42
<212> TYPE: DNA
<213> ORGANISM: Artificial
<220> FEATURE:
<223> OTHER INFORMATION: Artificial nucleic acid encoding polypeptide of the invention

<400> SEQUENCE: 68
cgtactcgta aacgtggtcg tcgtactcgt aaacgtggtc gt 42

<210> SEQ ID NO 69
<211> LENGTH: 42
<212> TYPE: DNA
<213> ORGANISM: Artificial
<220> FEATURE:
<223> OTHER INFORMATION: Artificial nucleic acid encoding polypeptide of the invention

<400> SEQUENCE: 69
cttcgtaaac gtaaacgtct tcttcgtaaa cgtaaacgtc tt 42

<210> SEQ ID NO 70
<211> LENGTH: 54
<212> TYPE: DNA
<213> ORGANISM: Artificial
<220> FEATURE:
<223> OTHER INFORMATION: Artificial nucleic acid encoding polypeptide of the invention

<400> SEQUENCE: 70
cttcgtaaac gtaaacgtct tcgtaaactt cgtaaacgta aacgtcttcg taaa 54

<210> SEQ ID NO 71
<211> LENGTH: 54
<212> TYPE: DNA
<213> ORGANISM: Artificial
<220> FEATURE:
<223> OTHER INFORMATION: Artificial nucleic acid encoding polypeptide of the invention

<400> SEQUENCE: 71
tggcgttggc gtaaacgttg gcgtaaatgg cgttggcgta aacgttggcg taaa 54

<210> SEQ ID NO 72
<211> LENGTH: 54
<212> TYPE: DNA
<213> ORGANISM: Artificial
<220> FEATURE:
<223> OTHER INFORMATION: Artificial nucleic acid encoding polypeptide designated MU 4

<400> SEQUENCE: 72
tggcgtaaat ggcgtaaacg ttggtggtgg cgtaaatggc gtaaacgttg gtgg 54

<210> SEQ ID NO 73
<211> LENGTH: 54
<212> TYPE: DNA
<213> ORGANISM: Artificial
<220> FEATURE:
<223> OTHER INFORMATION: Artificial nucleic acid encoding polypeptide designated MU 7

<400> SEQUENCE: 73
tttcgtaaat ttcgtaaacg tttttttttt cgtaaatttc gtaaacgttt tttt 54

<210> SEQ ID NO 74
<211> LENGTH: 54
<212> TYPE: DNA
<213> ORGANISM: Artificial
<220> FEATURE:
<223> OTHER INFORMATION: Artificial nucleic acid encoding polypeptide designated MU 10

<400> SEQUENCE: 74
ttacgtaaat tacgtaaacg tttattatta cgtaaattac gtaaacgttt atta 54

<210> SEQ ID NO 75
<211> LENGTH: 54
<212> TYPE: DNA
<213> ORGANISM: Artificial
<220> FEATURE:
<223> OTHER INFORMATION: Artificial nucleic acid encoding polypeptide designated MU 114

<400> SEQUENCE: 75
tggcgtaaat ggcgtaaacg tttattatta cgtaaattac gtaaacgttt atta 54

<210> SEQ ID NO 76
<211> LENGTH: 18
<212> TYPE: PRT
<213> ORGANISM: Artificial
<220> FEATURE:
<223> OTHER INFORMATION: Artificial polypeptide designated MU 1

<400> SEQUENCE: 76

Glu Arg Lys Glu Arg Lys Arg Glu Glu Glu Arg Lys Glu Arg Lys Arg
1 5 10 15

Glu Glu

<210> SEQ ID NO 77
<211> LENGTH: 18
<212> TYPE: PRT
<213> ORGANISM: Artificial
<220> FEATURE:
<223> OTHER INFORMATION: Artificial polypeptide designated MU 2

<400> SEQUENCE: 77

Ala Arg Lys Ala Arg Lys Arg Ala Ala Ala Arg Lys Ala Arg Lys Arg
1 5 10 15

Ala Ala

<210> SEQ ID NO 78
<211> LENGTH: 18
<212> TYPE: PRT
<213> ORGANISM: Artificial
<220> FEATURE:
<223> OTHER INFORMATION: Artificial polypeptide designated MU 3

<400> SEQUENCE: 78

Asp Arg Lys Asp Arg Lys Arg Asp Asp Asp Arg Lys Asp Arg Lys Arg
1 5 10 15

Asp Asp

<210> SEQ ID NO 79
<211> LENGTH: 18
<212> TYPE: PRT
<213> ORGANISM: Artificial
<220> FEATURE:
<223> OTHER INFORMATION: Artificial polypeptide designated MU 9

<400> SEQUENCE: 79

Gln Arg Lys Gln Arg Lys Arg Gln Gln Gln Arg Lys Gln Arg Lys Arg
1 5 10 15

Gln Gln

<210> SEQ ID NO 80

<211> LENGTH: 18
<212> TYPE: PRT
<213> ORGANISM: Artificial
<220> FEATURE:
<223> OTHER INFORMATION: Artificial polypeptide designated MU 11

<400> SEQUENCE: 80

Asn Arg Lys Asn Arg Lys Arg Asn Asn Asn Arg Lys Asn Arg Lys Arg
1 5 10 15

Asn Asn

<210> SEQ ID NO 81
<211> LENGTH: 18
<212> TYPE: PRT
<213> ORGANISM: Artificial
<220> FEATURE:
<223> OTHER INFORMATION: Artificial polypeptide designated MU 13

<400> SEQUENCE: 81

Ser Arg Lys Ser Arg Lys Arg Ser Ser Ser Arg Lys Ser Arg Lys Arg
1 5 10 15

Ser Ser

<210> SEQ ID NO 82
<211> LENGTH: 18
<212> TYPE: PRT
<213> ORGANISM: Artificial
<220> FEATURE:
<223> OTHER INFORMATION: Artificial polypeptide designated MU 14

<400> SEQUENCE: 82

Val Arg Lys Val Arg Lys Arg Val Val Val Arg Lys Val Arg Lys Arg
1 5 10 15

Val Val

<210> SEQ ID NO 83
<211> LENGTH: 18
<212> TYPE: PRT
<213> ORGANISM: Artificial
<220> FEATURE:
<223> OTHER INFORMATION: Artificial polypeptide designated MU 15

<400> SEQUENCE: 83

Thr Arg Lys Thr Arg Lys Arg Thr Thr Thr Arg Lys Thr Arg Lys Arg
1 5 10 15

Thr Thr

<210> SEQ ID NO 84
<211> LENGTH: 18
<212> TYPE: PRT
<213> ORGANISM: Artificial
<220> FEATURE:
<223> OTHER INFORMATION: Artificial polypeptide designated MU 17

<400> SEQUENCE: 84

Gly Arg Lys Gly Arg Lys Arg Gly Gly Gly Arg Lys Gly Arg Lys Arg
1 5 10 15

Gly Gly

<210> SEQ ID NO 85
<211> LENGTH: 18
<212> TYPE: PRT
<213> ORGANISM: Artificial
<220> FEATURE:

<223> OTHER INFORMATION: Artificial polypeptide designated MU 18

<400> SEQUENCE: 85

Lys Arg Lys Lys Arg Lys Arg Lys Lys Lys Arg Lys Lys Arg Lys Arg
1 5 10 15

Lys Lys

<210> SEQ ID NO 86
<211> LENGTH: 18
<212> TYPE: PRT
<213> ORGANISM: Artificial
<220> FEATURE:
<223> OTHER INFORMATION: Artificial polypeptide designated MU 20

<400> SEQUENCE: 86

Pro Arg Lys Pro Arg Lys Arg Pro Pro Pro Arg Lys Pro Arg Lys Arg
1 5 10 15

Pro Pro

<210> SEQ ID NO 87
<211> LENGTH: 9
<212> TYPE: PRT
<213> ORGANISM: Artificial
<220> FEATURE:
<223> OTHER INFORMATION: Artificial polypeptide designated MU 45

<400> SEQUENCE: 87

Trp Arg Lys Trp Arg Lys Arg Trp Trp
1 5

<210> SEQ ID NO 88
<211> LENGTH: 18
<212> TYPE: PRT
<213> ORGANISM: Artificial
<220> FEATURE:
<223> OTHER INFORMATION: Artificial polypeptide designated MU 25

<400> SEQUENCE: 88

Trp Arg Trp Arg Arg Arg Trp Arg Lys Trp Arg Trp Arg Arg Arg Trp
1 5 10 15

Arg Lys

<210> SEQ ID NO 89
<211> LENGTH: 18
<212> TYPE: PRT
<213> ORGANISM: Artificial
<220> FEATURE:
<223> OTHER INFORMATION: Artificial polypeptide designated MU 26

<400> SEQUENCE: 89

Trp Arg Trp Lys Lys Lys Trp Arg Lys Trp Arg Trp Lys Lys Lys Trp
1 5 10 15

Arg Lys

<210> SEQ ID NO 90
<211> LENGTH: 18
<212> TYPE: PRT
<213> ORGANISM: Artificial
<220> FEATURE:
<223> OTHER INFORMATION: Artificial polypeptide designated Formula I
<220> FEATURE:
<221> NAME/KEY: misc_feature
<222> LOCATION: (1)..(1)
<223> OTHER INFORMATION: Xaa can be Arg, Tyr, Met, Ile, leu, Phe, Try, Leu, Lys, His, Cys, or deleted -continued

```
<220> FEATURE:
<221> NAME/KEY: misc_feature
<222> LOCATION: (2)..(2)
<223> OTHER INFORMATION: Xaa can be Arg, Tyr, Met, Ile, Phe, Try, Leu,
      Lys, Cys, or deleted
<220> FEATURE:
<221> NAME/KEY: misc_feature
<222> LOCATION: (3)..(3)
<223> OTHER INFORMATION: Xaa can be Arg, Tyr, Met, Ile, Phe, Try, Leu,
      Lys, His, Thr, Cys, or deleted
<220> FEATURE:
<221> NAME/KEY: misc_feature
<222> LOCATION: (7)..(7)
<223> OTHER INFORMATION: Xaa can be Arg, Tyr, Met, Ile, Phe, Try, Leu,
      Lys, His, Gly, Cys, or deleted
<220> FEATURE:
<221> NAME/KEY: misc_feature
<222> LOCATION: (8)..(8)
<223> OTHER INFORMATION: Xaa can be Arg, Tyr, Met, Ile, Phe, Try, Leu,
      Lys, His, Cys, or deleted
<220> FEATURE:
<221> NAME/KEY: misc_feature
<222> LOCATION: (9)..(9)
<223> OTHER INFORMATION: Xaa can be Arg, Tyr, Met, Ile, Phe, Try, Leu,
      Lys, His, Cys, or deleted
<220> FEATURE:
<221> NAME/KEY: misc_feature
<222> LOCATION: (10)..(10)
<223> OTHER INFORMATION: Xaa can be Arg, Tyr, Met, Ile, leu, Phe, Try,
      Leu, Lys, His, Cys, or deleted
<220> FEATURE:
<221> NAME/KEY: misc_feature
<222> LOCATION: (11)..(11)
<223> OTHER INFORMATION: Xaa can be Arg, Tyr, Met, Ile, Phe, Try, Leu,
      Lys, Cys, or deleted
<220> FEATURE:
<221> NAME/KEY: misc_feature
<222> LOCATION: (12)..(12)
<223> OTHER INFORMATION: Xaa can be Arg, Tyr, Met, Ile, Phe, Try, Leu,
      Lys, His, Thr, Cys, or deleted
<220> FEATURE:
<221> NAME/KEY: misc_feature
<222> LOCATION: (16)..(16)
<223> OTHER INFORMATION: Xaa can be Arg, Tyr, Met, Ile, Phe, Try, Leu,
      Lys, His, Gly, Cys, or deleted
<220> FEATURE:
<221> NAME/KEY: misc_feature
<222> LOCATION: (17)..(17)
<223> OTHER INFORMATION: Xaa can be Arg, Tyr, Met, Ile, Phe, Try, Leu,
      Lys, His, Cys, or deleted
<220> FEATURE:
<221> NAME/KEY: misc_feature
<222> LOCATION: (18)..(18)
<223> OTHER INFORMATION: Xaa can be Arg, Tyr, Met, Ile, Phe, Try, Leu,
      Lys, His, Cys, or deleted

<400> SEQUENCE: 90

Xaa Xaa Xaa Arg Lys Arg Xaa Xaa Xaa Xaa Xaa Xaa Arg Lys Arg Xaa
1               5                   10                  15

Xaa Xaa
```

TREATMENT OF FUNGAL AND/OR PROTIST INFECTIONS

This application claims the benefit of priority under 35 U.S.C. §120 as a continuation of a U.S. patent application Ser. No. 11/916,627, filed Dec. 5, 2007, which is a National Phase of International Application PCT/GB06/02350, filed Jun. 26, 2006, which designated the U.S. and that International Application was published under PCT Article 21(2) in English. This application also includes a claim of priority under 35 U.S.C. §119(a) and §365(b) to British patent application No. GB0513096.8, filed Jun. 28, 2005.

The present invention relates to polypeptides, derivatives or analogues thereof, with antimicrobial activity, and to nucleic acids encoding the same. More specifically, the invention relates to polypeptides, derivatives or analogues thereof with antifungal and/or antiprotist activity. The invention further provides the use of such polypeptides, derivatives, analogues or nucleic acids as medicaments, and also in methods of treatment. The invention further extends to objects and surfaces coated with the polypeptides.

Antimicrobial, peptides are a key component of the innate immune system, generally containing 20-40 amino acids, having a net positive charge, and with the majority having been identified so far in non-mammalian species. Both of these factors limit their usefulness as therapeutics in humans or mammals. This is due to difficulties in commercial production of such large peptides, and the risk of adverse effects from peptides of non-human origin. By 2006, of the around 890 sequences listed in the Trieste international antimicrobial peptide database (http://www.bbcm.units.it/~tossi/amsd-b.html), only 35 were of human origin, and of these only 3 are less than 20 amino acids in length. Some short synthetic antimicrobial peptides have also been developed. However, these have the disadvantage of associated risks of antigenic or toxic effects due to their non-human origin.

Such peptides have been, characterised into six groups (Bradshaw, J. P., Biodrugs, 2003: 17: 235-240), with the following three classes being most studied (Bowman H. G., Journal of Internal Medicine, 2003: 254:197-215);

(i) Linear peptides lacking cysteines and often with an α-helical amphipathic structure in solution, for example, Human LL-37 (SEQ ID No 1): LLGDFFRKSKEKIGKEFKRI VQRIKDFLRN LVPRTES;

(ii) Peptides with 3 disulphide bonds, giving peptides with a flat dimeric beta-sheet, for example, Human α-defensin: HNP-1 (SEQ ID No.2)

ACYCRIPACI AGERRYGTCI YQGRLWAFCC (iii) Peptides with unusual bias in certain amino acids such as proline, arginine, tryptophan or histidine, for example, Pig PR-39 (SEQ ID No.3): RRRPRPPYLP RPRPPPFFPP RLPPRIPPGF PPRFPPRFP; or cow indolicidin (SEQ ID No.4): ILPWKWPWWP WRR.

Some peptides have been discovered that have the capacity to inhibit the growth of fungi. Examples of such peptides include Cecropins, Buforins, Pleuoridin Pyrrhocoricin, metalnikowin, sheperins, AcAMP1 and Ac-AMP2, Histatins, Tachyplesin II, Androctonin, Protegrin I, α Defensins and β Defensins, Penaeidins, Tachycitin, Heliomicin, defensin protein WT1, alfAFP defensin, So-d1-7, DmAMP1. Furthermore, some peptides have been found to additionally inhibit protozoa (for example Megainin, and dermaseptin). Others have been shown to inhibit both fungi and protozoa (for example Gambicin). However, at present, the mechanism of such agents to impart their antifungal and/or antiprotozoan activities is not fully understood.

A number of antibacterial peptides that have been described in the scientific literature have strong cationic character, and often consist of arginine and lysine residues. However, not all peptides containing arginine and lysine have antimicrobial activity. For example, Azuma et al. (Peptides, 21: 327-330 (2000)) have reported that peptide derivatives of apolipoprotein E have a strong antibacterial action, comparable to that of gentamicin. However, Azuma's peptide, $apoE_{134-151}$(18 amino acids in length) had no activity at all despite containing arginines both at positions 142 and 147. Similarly, Azuma demonstrated that the peptide $apoE_{134-155}$ (22 amino acids in length) had very low antibacterial activity, and the peptide $apoE_{134-159}$ (26 amino acids in length) had greatly reduced antibacterial activity. Finally, Azuma et al. only investigated the antibacterial activity of the apoE derived peptides, and did not evaluate any other anti-microbial effects, for example, activity against fungi or protists.

Following on from the research carried out by Azuma et. al., the inventor of the present invention investigated the action of certain polypeptides based on apolipoproteins B and E, against viruses. The inventor established that certain polypeptides do have antiviral activity. The results of his research are described in PCT/GB2004/005438 and PCT/GB2004/005360. These antiviral polypeptides comprise tandem repeats, and variants thereof, of the peptides: $apoE_{141-149}$ (LRKLRKRLL—SEQ ID No.5) and $apoB_{3359-3367}$ (RLTRKRGLK—SEQ ID No.6) as-well-as repeats of closely related modifications of SEQ ID No.5 or SEQ ID No.6. These peptides are either derived from or comprise the LDL receptor/HSPG receptor binding region of apolipoproteins E and B. While the inventor does, not wish to be bound by any hypothesis, he considers it likely that these antiviral polypeptides exert their antiviral actions by a number of mechanisms, with those affecting viral attachment being particularly favoured. The inventor suggests that dimerisation of peptides derived from the LDL receptor/HSPG receptor binding region of these apolipoproteins (as a tandem repeat or variants thereof) is important for an antiviral effect.

Despite the fact that antiviral agents are unrelated to antibacterial agents due to their different modes of action on viruses and bacteria, respectively, the inventor also decided to investigate whether polypeptides, based on the antiviral peptides discussed above, also had any antibacterial properties. The results of this research are described in PCT/GB2005/000769. To his surprise, the inventor found that in addition to antiviral activity, these polypeptides also exhibited antibacterial activity.

The inventor of the present invention continued his investigations on these polypeptides based on apolipoproteins B and E. Accordingly, despite the fact that antiviral agents, and antibacterial agents are unrelated to antifungal agents and agents exhibiting activity to other micro-organisms, due to their different modes of action on viruses, bacteria, and fungi, respectively, the inventor of the present invention also decided to investigate whether polypeptides, based on the antiviral/antibacterial peptides discussed above, had any antifungal properties, or exhibited any activity against any other micro-organisms.

Specifically, the inventor wondered whether construction of a repeat (e.g. tandem repeats) of peptides derived from the LDL receptor/HSPG receptor binding region of these apolipoproteins may have other antimicrobial effects, for example, against fungi or other micro-organisms, such as protozoa. In particular, the inventor wondered if repeats of the apo$E_{141-149}$ region might unexpectedly exhibit either antifungal and/or antiprotist activity. To his surprise, he found that polypeptides, as defined below, do exhibit antifungal activity, and also activity against other micro-organisms, in addition to the antiviral and antibacterial activities, which had been demonstrated previously.

According to a first aspect of the present invention, there is provided use of a polypeptide, or a derivative or analogue thereof, comprising repeats of a peptide derived from a Heparan Sulphate Proteoglycan (HSPG) receptor binding region of an apolipoprotein for the manufacture of a medicament for the treatment of a fungal and/or protist infection.

By the term "derivative or analogue thereof", we mean a polypeptide within which amino acids, residues are replaced by residues (whether natural amino acids, non-natural amino acids or amino acid mimics) with similar side chains or peptide backbone properties. Additionally, either one or both terminals of such peptides may be protected by N and C-terminal protecting groups, for example, groups with similar properties to acetyl or amide groups. It will be appreciated that the amino acid sequence may be varied, truncated or modified once the final polypeptide is formed or during the development of the repeated peptides (e.g. the 9-mer).

Preferably, the polypeptide of the invention comprises at least two repeats of a peptide derived from an HSPG receptor binding region of an apolipoprotein. It will be appreciated that the polypeptide may comprise repeats of the same peptide (i.e. a homodimer or polymer of the same peptide). Alternatively, the polypeptide may comprise a repeat of two or more related peptides (i.e. a heterodimer or a polymer comprising two or more peptide types of peptide monomer). If the polypeptide comprises different peptides, it will be appreciated that such peptides will share the characteristics that they are, or are derived from, an HSPG receptor binding region of an apolipoprotein, as defined in the first aspect of the invention.

It is preferred that polypeptides according to the invention comprise dimers or polymers of such peptides linked N terminal to C terminal in a fashion that would be known to one skilled in the art as a tandem repeat. Accordingly, unless the context dictates otherwise, when we refer to "tandem repeats" herein, we mean a repeat of peptides that are, or are derived from, an HSPG receptor binding region of an apolipoprotein. Such tandem repeats may be homodimers (or polymers of a single peptide) or may comprise a heterodimer (or polymer of related peptides) as discussed above.

The term "peptides derived from" as used herein is intended to describe or include peptides from the HSPG receptor binding region of an apolipoprotein that have been modified. Suitable modification may include amino acid substitution, addition or deletion. The derivative peptide or modified peptide is arranged as a tandem repeat in accordance with the first aspect of the invention. Surprisingly, and completely contrary to expectation, polypeptides, derivatives or analogues thereof according to the first aspect of the invention have been shown to exhibit antifungal and/or antiprotist activity.

When the term "a truncation thereof" is used herein, we mean that the polypeptide according to the invention or the constituent peptide is reduced in size by removal or deletion of one or more amino acids. The reduction of amino acids may be by removal of residues from the C or N terminal of the polypeptide, or may be by deletion of one or more amino acids from within the constituent peptides.

The inventors have previously found that polypeptides as defined above have antiviral and antibacterial activity. However, to the inventors' surprise, when the polypeptides according to the first aspect were tested on fungi and protists, they also showed antifungal efficacy and also activity against protists, as shown in the Examples. Hence, it is the inventors' belief that they have therefore shown a new medical indication for these polypeptides.

The medicament according to the first aspect of the invention may be used in the medical treatment of humans or for veterinary use. The medicament is preferably used to treat fungal infections of humans and other mammals.

The polypeptide used to prevent or treat fungal and/or protist infections is preferably derived from the same species as the subject being treated. When that subject is a human it is preferred that the polypeptide is based on repeats derived from human apolipoproteins.

By the term "fungal infection", we mean an infection with, or caused by, a fungus. Infections that may be treated include: blastomycosis, coccidiodomycosis, cryptococcosis, histoplasmosis, sporotrichosis, chromoblastomycosis, lobomycosis, dermatophytosis, dermatomycosis, onychomycosis, piedra, mycetoma, fusariosis, pityriasis versicolor, tinea barbae, tinea capitis, tinea corporis, tinea cruris, tinea favosa, tinea nigra, tinea pedis, phaeohyphomycosis, rhinosporidiosis, aspergillosis, mycotic keratitis, candidiasis.

By the term "protist infection", we mean an infection with, or caused by, a protist. Diseases caused by infection with Protista include giardiasis and other gastrointestinal disorders including amoebic dysentery and diarrhoea, cutaneous and visceral leishmaniasis, Chagas' disease, coccidiosis, ick, trichomoniasis, African sleeping, sickness, red tides, toxoplasmosis, malaria, and microbial keratitis, including *Acanthamoeba* keratitis.

In general, antiviral agents, such as acyclovir, ribavirin, or enfuvirtide (T-20), are rarely useful against antifungal infections due to their completely different modes of action. Similarly, antifungal agents, such as Butenafine, Butoconazole, or Naftifine, are rarely useful against viral infections. Accordingly, the inventor of the present invention was very surprised that the polypeptides according to the first aspect of the invention showed antiviral, and antibacterial efficacy, and also activity against fungal and/or protist infections. It was completely unexpected that the peptides according to the invention would have activity across kingdoms, i.e. activity in the Kingdom Monera (bacteria and viruses), and the Kingdom Fungi, and also the Kingdom Protista. The inventor was surprised that the peptides according to the invention had such versatility and such a broad range of activity, as this very rarely occurs.

Whilst the inventor does not wish to be bound by any hypothesis, he has suggested that the antifungal/antiprotist mechanism of action by the polypeptides in accordance with the invention, may involve a direct damaging effect to the fungus or protist, either mediated through the membrane, or through targeting a site within the fungus or protist. In addition, blockade of attachment or entry of intracellular parasites (e.g. *Plasmodium*) into host cells is also possible. It is possibly for these reasons that only a surprisingly small number of peptide sequences (i.e. those defined by the first aspect of the invention) have been found to be effective against fungi and/or protists.

The majority of the polypeptides according to the invention were surprisingly active as both antifungal and/or antiprotist agents, and also antiviral agents and antibacterial agents. It is possible that in some embodiments of the invention, the peptides may exhibit combinations of the above antimicrobial activities. For example, the peptides may exhibit either antifungal or antiprotist activity (and various combinations of antibacterial and antiviral activity). Preferred polypeptides according to the first aspect exhibit antifungal and antiprotist activity and in addition antibacterial activity and/or antiviral activity. It will be apparent that this quadruple activity exhibited by the polypeptides is most advantageous, as they may be used to prevent or treat fungal infections, protist infections and also viral and bacterial infections, preferably, simultaneously.

The polypeptides according to the first aspect of the invention may comprise repeats of peptides derived from a Heparan Sulphate Proteoglycan (HSPG) receptor binding region of human apolipoprotein B or human apolipoprotein E. It is preferred that the polypeptide according to the first aspect of the invention comprises a tandem repeat (as defined above) of peptides derived from an apolipoprotein B LDL receptor binding domain cluster B, as defined by Law and Scott (J. Lipid Res. 1990, 31:1109-20), or alternatively, from an apolipoprotein E LDL receptor binding domain cluster B (J. Lipid Res. 1995, 36:1905-1918). The apolipoprotein B LDL receptor binding domain cluster B may be located within an HSPG receptor binding region of apolipoprotein B, and the apolipoprotein E LDL receptor binding domain cluster B of apolipoprotein E may be located within an HSPG binding domain of apolipoprotein E.

The inventor conducted exhaustive experiments to assess the antifungal and antiprotist activity of peptides from apolipoproteins and derivatives thereof. Peptides and derivatives from ApoE and ApoB were a particular focus. The inventor found that the $apoE_{141-149}$ monomeric sequence (see Table 1 and SEQ ID No.5); the $apoB_{3359-3367}$ (see Table 1 and SEQ ID No. 6) and the modified $apoB_{3359-3367}$ (see Table 1 and SEQ ID No.7) had no detectable antifungal activity. However, surprisingly, the inventor found that repeats of such peptides (i.e. polypeptides in accordance with the first aspect of the present invention), do exhibit antifungal and/or antiprotist activity. Examples 1 and 4 illustrate the antifungal efficacy of the polypeptides according to the invention, and Examples 2 and 5 illustrate the antiprotist activity of the polypeptides according to the invention.

While the inventor does not wish to be bound by any hypothesis, the inventor believes that the cationic amino acid residues in the $apoE_{141-149}$ peptides (based on SEQ ID No.5) and $apoB_{3359-3367}$ peptides (based on SEQ ID No.6) and modified $apoB_{3359-3367}$ peptides (based on SEQ ID No.7) when in the form of tandem repeats allows antifungal activity and antiprotist activity to occur. The inventor has also established that certain derivatives of these peptides also have antifungal and/or antiprotist activity, including modifications and truncations of the peptide sequences.

The inventor carried out some detailed analysis of polypeptides with antifungal and antiprotist activity and in particular those based on repeats of peptides derived from the Heparan Sulphate Proteoglycan (HSPG) receptor binding region of apolipoprotein B or apolipoprotein E. The inventor produced a sequence alignment between the amino acids of $apoE_{141-149}$ (i.e. the 9-mer of SEQ ID No.5), aligned with the amino acids of $apoB_{3359-3367}$ (i.e. the 9-mer of SEQ ED No. 6), and also the modified form of $apoB_{3359-3367}$ (i.e. the 9-mer of SEQ ID No.7). The sequence alignment is shown in Table 1. It will be appreciated that these three 9-mers, or derivatives thereof, are repeated in the polypeptides according to the present invention to form at least an 18-mer, which may be optionally truncated.

TABLE 1

Analysis of effective peptide sequences exhibiting antifungal/antiprotist properties

| 0 | 1 | 2 | 3 | 4 | 5 | 6 | 7 | 8 | 9 | |
|---|---|---|---|---|---|---|---|---|---|---|
| L | R | K | L | R | K | R | L | L | - | apoE (141-149) - SEQ ID No. 5 |
| - | R | L | T | R | K | R | G | L | K | apoB (3359-3367) - SEQ ID No. 6 |
| - | L | R | T | R | K | R | G | R | K | Modified apoB (3359-3367) - SEQ ID No. 7 |

Indicates residue is the same residues in apoB 3359-3367 and apoE (141-149)

In the light of this alignment data, the inventor noticed that there was a recurring (conserved) amino acid motif in each of the antifungal polypeptides comprising tandem repeats of a peptide derived from a Heparan Sulphate Proteoglycan (HSPG) receptor binding region of apolipoprotein B ($apoB_{3359-3367}$ (SEQ ID No.6)), or the modified apolipoprotein B ($apoB_{3359-3367}$ (SEQ ID No.7)), or apolipoprotein ($apoE_{141-149}$ (SEQ ID No.5)), or a truncation thereof. This motif corresponds to a tripeptide: Arginine-Lysine-Arginine (RKR), which is found at amino acid residues designated: 4, 5, 6 of SEQ ID. No.5, and SEQ ID No.7, and SEQ ID No.6. The inventor noticed that all of the polypeptides according to the invention exhibiting antifungal and/or antiprotist activity comprise these RKR motifs.

Therefore, it is especially preferred that the polypeptide according to the invention comprises at least two RKR motifs (i.e. the polypeptide comprises a tandem repeat of peptides comprising RKR motifs).

It will be appreciated that polypeptides according to the present invention comprise at least two or more RKR motifs (i.e. one RKR motif per repeat). In situations where the polypeptide comprises a trimer (3×) repeat, or tetramer (4×) repeat, or an even greater number of repeat, the polypeptide preferably comprises at least three, or at least four RKR motifs, respectively.

Preferred peptides comprise two RKR motifs and consist of 18 amino acid or less.

In one embodiment of the invention, the polypeptide according to the first aspect may comprise a dimer repeat of the peptide comprising the RKR motif and preferably has formula I:

{abcRKRxyz}+{a'b'c'RKRx'y'z'} wherein a, b, c, a', b', c', x, y, z, x', y', z' are amino, acid residues, and wherein the polypeptide comprise peptide abcRKRxyz and peptide a'b'c'RKRx'y'z' which are repeats of SEQ ID No.5, SEQ ID No.6, or SEQ ID No.7 and derivatives thereof. Such derivatives may comprise SEQ ID No.5, SEQ ID No.6, or SEQ ID No.7, wherein at least one amino acid residue of that peptide, other than the RKR motifs, may be replaced by an Arginine (R), Tyrosine (Y), Methionine (M), Isoleucine (I), Phenylalanine (F), Tryptophan (W), Cysteine (C) or a derivative thereof. The peptide may also comprise a Histidine (H) substitution.

It is preferred that amino acid substitutions are with a Arginine (R), Phenylalanine (F) or Tryptophan (W) residue and most preferably, a Tryptophan (W) residue, or a derivative thereof Suitably, one or more, more suitably, two or more, and even more suitably, three or more amino acid residues may be replaced by an Arginine (R), Tyrosine (Y), Methionine (M), Isoleucine (I), Phenylalanine (F), Tryptophan (W), Cysteine (C) or derivative thereof. In one embodiment of the invention it is preferred that four or more, more preferably, five or more, and even more preferably, six or more amino acid residues of the polypeptide according to the first aspect of the invention may be replaced by these amino acids or a derivative thereof. Preferably, the replaced or substituted residue is the first, second, third, seventh, eighth, ninth, tenth, eleventh, twelfth, sixteenth, seventeenth or eighteenth residue of the peptide defined by formula I.

The polypeptide according to the invention may comprise 18 amino acids (or derivatives thereof), and thereby correspond to the sequence defined by formula I with or without the substitutions discussed above. In this case, amino acid position 1 corresponds to a; position 2 corresponds to b; position 3 corresponds to c, position 4 corresponds to the amino acid R (of the RKR motif), and so on.

However, the inventor has surprisingly found that truncated polypeptides based on formula I also have efficacy as antifungal agents, and/or antiprotist agents. Accordingly, preferred polypeptides or derivatives thereof may have less than 18 amino acids. For instance, some polypeptides according to the first aspect of the invention may be 17, 16, 15, 14, 13, 12, 11, 10 or less amino acids in length. Deletions are preferably made at positions 1, 2, 8, 9, 10, 11, 17 and/or 18 of the polypeptide defined by formula I.

The inventor has also surprisingly found that polypeptides based on formula I but having additional amino acid residues, also have efficacy as antifungal/antiprotist agents. Accordingly, preferred polypeptides or derivatives thereof may have greater than 18 amino acids. For instance, some polypeptides according to the first aspect of the invention may be 19, 20, 21, 22, 23, 24, 25, 26, 27, 28, 29 or more amino acids in length. Additions may be made to the N or C-terminal, or in the core of the polypeptide. Additions may be made either before residue 'a' (i.e. at the N-terminal end of the polypeptide), or before 'a'' (i.e. in the core of the polypeptide), as defined in formula I. Additions may be made either after residue 'z' (i.e. in the core of the peptide) or after 'z'' (at the C-terminal end of the peptide), as defined in formula I.

However, the addition is preferably made at position 0, 1, 2, 8, 9, 10, 11, 17 and/or 18 of the peptide defined by formula I. Most preferably, additions are made before position 0 of the peptide, i.e. amino acids are added to the N-terminal before the first amino acid at residue 'a' defined by formula I.

The polypeptide according to formula I may preferably comprise the following amino acids:

a & a'=is independently selected from Arginine (R); Tyrosine (Y); Methionine (M); Isoleucine (I); Phenylalanine (F); Tryptophan (W); Leucine (L); Lysine (K); Histidine (H); Cysteine (C); or is deleted;

b & b'=is independently selected from Arginine (R); Tyrosine (Y); Methionine (M); Isoleucine (I); Phenylalanine (F); Tryptophan (W); Leucine (L); Lysine (K); Cysteine (C); or is deleted;

c & c'=is independently selected from Arginine (R); Tyrosine (Y); Methionine (M); Isoleucine (I); Phenylalanine (F); Tryptophan (W); Leucine (L); Lysine (K); Histidine (H); Cysteine (C); Threonine (T); or is deleted;

x & x'=is independently selected from Arginine (R); Tyrosine (Y); Methionine (M); Isoleucine (I); Phenylalanine (F); Tryptophan (W); Leucine (L); Lysine (K); Histidine (H); Cysteine (C), Glycine (G); or is deleted;

y & y'=is independently selected from Arginine (R); Tyrosine (Y); Methionine (M); Isoleucine (I); Phenylalanine (F); Tryptophan (W); Leucine (L); Lysine (K); Cysteine (C); Histidine (H); or is deleted;

z & z'=is independently selected from Arginine (R); Tyrosine (Y); Methionine (M); Isoleucine (I); Phenylalanine (F); Tryptophan (W); Leucine (L); Lysine (K); Cysteine (C); Histidine (H); or is deleted.

The polypeptide of formula I may comprise at least one additional amino acid, which may be independently selected from Arginine (R); Tyrosine (Y); Methionine (M); Isoleucine (I); Phenylalanine (F); Tryptophan (W); Leucine (L); Lysine (K); Histidine (H). Preferably, the additional amino acid is added before the amino acid at position 'a' in the peptide of formula I, i.e. to the N-terminal.

Hence, it will be appreciated that the polypeptide according to the invention may comprise an 18-mer of {abcRKRxyz} and {a'b'c'RKRx'y'z'}, in which abc, a'b'c', xyz and x'y'z' are defined as above, or a truncation thereof. It will be appreciated that, for example, a may be different to a', and b may be different to b', and c may be different to c', and so on.

The polypeptide according to the first aspect may preferably be a homodimer of formula II:

{abcRKRxyz}+{abcRKRxyz} wherein a, b, c, x, y and z are as defined for formula I.

As with the polypeptide of formula I, the polypeptide of formula II may comprise at least one additional amino acid, which may be independently selected from Arginine (R); Tyrosine (Y); Methionine (M); Isoleucine (I); Phenylalanine (F); Tryptophan (W); Leucine (L); Lysine (K); Histidine (H). Preferably, the additional amino acid is added before the amino acid at position 'a' in the peptide of formula II, i.e. to the N-terminal.

Hence, it will be appreciated that the polypeptide according to the invention comprises an 18-mer of {abcRKRxyz} and {abcRKRxyz}, in which abc and xyz are defined as above, or a truncation thereof.

The polypeptide defined by formula II preferably comprises the following amino acids:

a=is independently selected from Arginine (R); Tyrosine (Y); Methionine (M); Isoleucine (I); Phenylalanine (F); Tryptophan (W); Cysteine (C); or is deleted;

b=is independently selected from Arginine (R); Tyrosine (Y); Methionine (M); Isoleucine (I); Phenylalanine (F); Tryptophan (W); Cysteine (C); or is deleted;

c=is independently selected from Phenylalanine (F); or Tryptophan (W); Cysteine (C); or is deleted;

x=is independently selected from Phenylalanine (F); Tryptophan (W); Cysteine (C); or is deleted;

y=is independently selected from Phenylalanine (F); Tryptophan (W); Cysteine (C); or is deleted;

z=is independently selected from Arginine (R); Tyrosine (Y); Methionine (M); Isoleucine (I); Phenylalanine (F); Tryptophan (W); Cysteine (C); or is deleted.

These preferred polypeptides may comprise at least one additional amino acid, which may be either Phenylalanine (F) or Tryptophan (W) or Leucine (L). Preferably, the additional amino acid is added before the amino acid at position 'a' in the polypeptide of formula II i.e. to the N-terminal.

The inventors have also appreciated that polypeptides may be employed according to the invention that comprise more than just a tandem dimer (2×) repeat of a peptide derived from a Heparan Sulphate Proteoglycan (HSPG) receptor binding region of apolipoprotein B or apolipoprotein E, or a truncation thereof. For example, polypeptides comprising a trimer (3×) repeat, or tetramer (4×) repeat, or an even greater number of repeats of a peptide derived from a Heparan Sulphate Proteoglycan (HSPG) receptor binding region, of apolipoprotein B or apolipoprotein E may be employed as useful antifungal and/or antiprotist agents.

Accordingly, it is preferred that the polypeptide may have formula III:

$$\{abcRKRxyz\}^n$$

wherein a, b, c, x, y, and z are as defined above with reference to formula I or II, and wherein n is equal to 2, 3, 4 or 5, or more.

Other preferred polypeptides may comprise repeats of the 18-mer peptide (or truncation thereof) defined by formula I (e.g. repeats of a heterodimer of the 9-mers comprising the peptide of formula I).

It is most preferred that the polypeptide according to the first aspect may comprise a repeat of $apoE_{141-149}$ (SEQ ID NO. 5), or derivatives and truncations thereof. Such peptides represent an important embodiment of the invention. Hence, in a second aspect, there is provided use of a polypeptide, derivative or analogue thereof comprising a repeat of the peptide $apoE_{141-149}$ (SEQ ID NO. 5) or a truncation thereof; or a repeat of a variant of the peptide $apoE_{141-149}$ in which at least one Leucine (L) residue is replaced by Tryptophan (W), Arginine (R), Lysine (K), Tyrosine (Y) Cysteine (C) or Phenylalanine (F), for the manufacture of a medicament for the treatment of a fungal and/or protist infection, or contamination.

By "a repeat of the peptide $apoE_{141-149}$", we mean a polypeptide comprising a repeat of the peptide sequence: LRKLRKRLL (SEQ ID No 5), i.e. a 9-mer. The polypeptide preferably comprises the amino acid sequence: LRKLRKRLLLRKLRKRLL (SEQ ID NO. 8), i.e. an 18-mer, which is a tandem repeat dimer of SEQ ID No.5. SEQ ID No. 8 is also referred to herein as GIN 1 or GIN1p (wherein p signifies N terminal protection (e.g. by an acetyl group), and C terminal protection (e.g. by an amide group)). GIN 1p is also referred to herein: as MU 10.

By "a truncation thereof", we mean that the repeat (e.g. the 18-mer of SEQ ID No.8) is reduced in size by removal of amino acids. The reduction of amino acids may be by removal of residues from the C- and/or N-terminal, or may be by deletion of one or more amino acids from within the core of the polypeptide (e.g. amino acids 2-17 of SEQ ID No.8).

The inventor has identified that Tryptophan (W), Arginine (R), Lysine (K), Tyrosine (Y), Cysteine (C) or Phenylalanine (F) may be substituted for Leucine in $apoE_{141-149}$ tandem repeats, and that such polypeptides have surprising antifungal/antiprotist activity.

It is more preferred that polypeptides according to the second aspect of the invention comprise a polypeptide, derivative or analogue thereof comprising a dimer repeat of $apoE_{141-149}$ or a truncation thereof, characterised in that at least one Leucine (L) residue of the dimer of SEQ ID No.8 is replaced by a Tryptophan (W), or a Phenylalanine (F) residue.

It is most preferred that at least one Leucine (L) residue of the dimer of SEQ ID No.8 is replaced by a Tryptophan (W) residue.

As discussed in more detail below, SEQ ID No.8 may be manipulated with a number of different substitutions and deletions to make polypeptides with antifungal and/or antiprotist activity. It is preferred that the polypeptide according to the second aspect of the invention has at least two substitutions independently selected from: Tryptophan (W), Arginine (R), Lysine (K), Tyrosine (Y), Cysteine (C) or Phenylalanine (F) substitutions, and more preferably three or more substitutions. It is preferred that these multiple substitutions are with Tryptophan (W), Arginine (R), Lysine (K), Tyrosine (Y), or Phenylalanine (F) and most preferred that there are multiple substitutions, with Tryptophan (W).

In addition to one or more L substitutions with K, R, Y, F, C or W, it is preferred that at least one further amino acid (preferably at least one further Leucine residue) is replaced with Arginine (R), Tyrosine (Y), Methionine (M), Isoleucine (I), Phenylalanine (F), or Tryptophan (W). It is particularly preferred that such a further substitution is F or W.

The inventor has also appreciated that polypeptides may be employed according to the invention that comprise more than just a dimer tandem repeat of $ApoE_{141-149}$ or a truncation or variant thereof. For instance, a timer or tetramer or greater number of repeats may be employed as antifungal and/or antiprotistagents.

The polypeptides according to the second aspect may be synthesised such that further amino acids are added thereto. For instance, one, two, three or more amino acids may be added to the C or N terminals of a peptide of SEQ ID No.8 or a derivative of such a peptide as defined above. Alternatively, the polypeptide may comprise a tandem repeat of a peptide that is larger than the nine amino acids of SEQ ID No.5. Such peptides may have amino acids added to the N terminal, C terminal and/or between the $9^{th}$ and $10^{th}$ amino acids of SEQ ID No. 8. It is most preferred that the amino acid is added to the C terminal and also between the $9^{th}$ and $10^{th}$ amino acids of SEQ ID No.8. It will be appreciated that such peptides, may then be modified as described above for polypeptides derived from SEQ ID No.8.

The substituted polypeptide may comprise 18 amino acids (or derivatives thereof) and thereby correspond to the full length of a dimer tandem repeat of $apoE_{141-149}$. However, the inventors have surprisingly found that some selected truncated polypeptides based on SEQ ID No.8 also have efficacy as antifungal and/or antiprotist agents. Accordingly, preferred polypeptides or derivatives thereof may have less than 18 amino acids. For instance, some polypeptides according to the second aspect of the invention may be 17, 16, 15, 14, 13, 12, 11, 10 or less amino acids in length.

It will be appreciated that modified forms of W, Y, R, K, C or F may be substituted into the tandem repeat of $apoE_{141-149}$ with a number of amino acid variants that may be known to those skilled in the art. Such polypeptides will still have antifungal and/or antiprotist activity provided that the modification does not significantly alter its chemical characteristics. For instance, hydrogens on the side chain amines of R or K may be replaced with methylene groups ($-NH_2 \rightarrow -NH(Me)$ or $-N(Me)_2$).

Other preferred polypeptides according to the second aspect of the invention (comprising tandem repeats of peptides derived from $apoE_{141-149}$) may comprise one of the following amino acid sequences:

(a) WRKWRKRWWWRKWRKRWW (SEQ ID No. 9). This polypeptide corresponds to a full length tandem dimer repeat of $apoE_{141-149}$ (SEQ ID NO. 8) with all Leucines substituted for Tryptophan residues. This polypeptide is designated GIN 7 or MU 4 when referred to herein.

(b) WRKWRKRWRKWRKR (SEQ ID No. 10). This polypeptide corresponds to the full length tandem dimer repeat of $apoE_{141-149}$ (SEQ ID NO. 8) with all Leucines substituted for Tryptophan residues and truncated by the excision of amino acids 9, 10, 17 and 18, i.e. is a 14-mer. This polypeptide is designated GIN 32 when referred to herein.

(c) WRKWRKRWWLRKLRKRLL (SEQ ID No. 11). This polypeptide corresponds to the full length tandem dimer repeat of $apoE_{141-149}$ (SEQ ID NO. 8) with a subset of Leucines substituted for Tryptophan residues, i.e. is an 18-mer. This polypeptide is designated GIN 34 when referred to herein.

(d) YRKYRKRYYYRKYRKRYY (SEQ ID No. 12). This polypeptide corresponds to the full length tandem dimer repeat of $apoE_{141-149}$ (SEQ ID NO. 8) with all Leucines substituted for tyrosine residues, i.e. is an 18-mer. This polypeptide is designated GIN 41 or MU6 when referred to herein.

(e) LRKLRKRLRKLRKR (SEQ ID No. 13). This polypeptide corresponds to the full length tandem dimer repeat of $apoE_{141-149}$ (SEQ ID NO. 8) truncated by the excision of amino acids 9, 10, 17 and 18, i.e. is an 14-mer. This polypeptide is designated GIN 8 when referred to herein.

(f) LRKRLLLRKLRKRLL (SEQ ID No.14). This polypeptide corresponds to the full length tandem dimer repeat of $apoE_{141-149}$ (SEQ ID NO. 8) truncated by the excision of amino acids 1, 2 and 3, i.e. is a 15-mer. This polypeptide is designated GIN 2 when referred to herein.

(g) FRKFRKRFFFRKFRKRFF (SEQ ID No.15). This polypeptide is designated MU 7 when referred to herein.

(h) WRKWRKRWWRKWRKRWW (SEQ ID NO.16). This polypeptide corresponds to SEQ ID No. 9 with the W residue at position 9 deleted. This polypeptide is designated MU 58 when referred to herein.

(i) WRKWRKRWRKWRKRW (SEQ ID NO.17). This polypeptide corresponds to SEQ ID No. 9 with the W residues at position 9, 10 and 18 deleted. This polypeptide is designated MU 59 when referred to herein.

(j) WRKWRKRWWFRKWRKRWW (SEQ ID NO.18). This polypeptide corresponds to SEQ ID No. 9 with the W residue at position 10 substituted with an F. This polypeptide is designated MU 60 when referred to herein.

(k) WRKWRKRFFWRKWRKRFF (SEQ ID NO.19). This polypeptide corresponds to SEQ ID No. 9 with the W residues at positions 9, 10, 17 and 18 substituted with F residues. This polypeptide is designated MU 61 when referred to herein.

(l) WRKRWWRWRKRWWR (SEQ ID NO.20). This polypeptide is designated MU 81 when referred to herein.

(m) LRKLRKRLLRLRKLRKRLLR (SEQ ID NO.21). This polypeptide is designated MU 82 when referred to herein.

(n) WRKWRKRWWRWRKWRKRWWR (SEQ ID NO.22). This polypeptide is designated MU 83 when referred to herein.

(o) LRKLRKRLLWRKWRKRWW (SEQ ID NO.23). This polypeptide corresponds to SEQ ID No. 8 with the L residues at positions 10, 13, 17 and 18 substituted with W residues. This polypeptide is designated MU 111 when referred to herein.

(p) LRKLRKRLLLRKLRKRWW (SEQ ID NO.24). This polypeptide corresponds to SEQ ID No. 8 with the L residues at positions 17 and 18 substituted with W residues. This polypeptide is designated MU 112 when referred to herein.

(q) LRKLRKRLLWRKWRKRLL (SEQ ID NO.25). This polypeptide corresponds to SEQ ID No. 8 with the L residues at positions 10 and 13 substituted with W residues. This polypeptide is designated MU 113 when referred to herein.

(r) WRKWRKRLLLRKLRKRLL (SEQ ID NO.26). This polypeptide corresponds to SEQ ID No. 8 with the L residues at positions 1 and 4 substituted with W residues. This polypeptide is designated MU 114 when referred to herein.

(s) WRKLRKRLLLRKLRKRLL (SEQ ID NO.27). This polypeptide corresponds to SEQ ID No. 8 with the L residue at position 1 substituted with W residues. This polypeptide is designated MU 115 when referred to herein.

(t) WRKWRKFFFRKWRKRWW (SEQ ID NO.28). This polypeptide corresponds to SEQ ID No. 9 with the W residues at positions 8, 9 and 10 substituted with F residues and the R residue at position 7 deleted. This polypeptide is designated MU 116 when referred to herein.

(u) WRKWRKRWWFRKFRKRFF (SEQ ID NO.29). This polypeptide corresponds to SEQ ID No. 9 with the W residues at positions 10, 13, 17 and 18 substituted with F residues. This polypeptide is designated MU 117 when referred to herein.

(v) CRKCRKRCCCRKCRKRCC (SEQ ID No. 30). This polypeptide corresponds to the full length tandem dimer repeat of $apoE_{141-149}$ (SEQ ID NO. 8) with all Leucines substituted for cysteine residues, i.e. is an 18-mer. This polypeptide is designated MU 12 when referred to herein.

(w) RRKRRKRRRRRKRRKRRR (SEQ ID No. 31). This polypeptide corresponds to the full length tandem dimer repeat of $apoE_{141-149}$ (SEQ ID NO. 8) with all Leucines substituted for arginine residues, i.e. is an 18-mer. This polypeptide is designated MU 16 when referred to herein.

(x) MRKMRKRMMMRKMRKRMM (SEQ ID No. 32). This polypeptide corresponds to the full length tandem dimer repeat of $apoE_{141-149}$ (SEQ ID NO. 8) with all Leucines substituted for methionine residues, i.e. is an 18-mer. This polypeptide is designated MU 5 when referred to herein.

(y) IRKIRKRIIIRKIRKRII (SEQ ID No. 33). This polypeptide corresponds to the full length tandem dimer repeat of $apoE_{141-149}$ (SEQ ID NO. 8) with all Leucines substituted for isoleucine residues, i.e. is an 18-mer. This polypeptide is designated MU 8 when referred to herein.

(z) HRKHRKRHHHRKHRKRHH (SEQ ID No. 34). This polypeptide corresponds to the full length tandem dimer repeat of $apoE_{141-149}$ (SEQ ID NO. 8) with all Leucines substituted for histidine residues, i.e. is an 18-mer. This polypeptide is designated MU 19 when referred to herein.

In most preferred embodiments, polypeptides according to the second aspect of the invention (comprising tandem repeats of peptides derived from, $apoE_{141-149}$) comprise one of the following amino acid sequences:

(i) WRKWRKRWWWRKWRKRWW (SEQ ID No. 9). This polypeptide corresponds to a full length tandem dimer repeat of $apoE_{141-149}$ (SEQ ID NO. 8) with all Leucines substituted for Tryptophan residues. This polypeptide is designated GIN 7 or MU 4 when referred to herein;

(ii) FRKFRKRFFFRKFRKRFF (SEQ ID No.15). This polypeptide is designated MU 7 when referred to herein;

(iii) LKRLRKRLLLRKLRKRLL (SEQ ID NO. 8), i.e. an 18-mer, which is a tandem repeat dimer of SEQ ID No.4. SEQ ID No. 8 is also referred to herein as GIN 1 or GIN1p (wherein p signifies N terminal protection (e.g. by an acetyl group), and C terminal protection (e.g. by an amide group). GIN 1p is also referred to herein as MU 10; and (iv) WRKWRKRLLLRKLRKRLL (SEQ ID NO.26). This polypeptide corresponds to SEQ ID No. 4 with the L residues at positions 1 and 4 substituted with W residues. This polypeptide is designated MU 114 when referred to herein.

Furthermore QSTEELRVRLASHLRKLRKRLL (SEQ ID No. 35), which contains only one RKR motif has been found to be a useful antifungal agent. This polypeptide is designated GIN 11 when referred to herein.

According to another embodiment of the first aspect of the invention preferred polypeptides comprise repeats of peptides derived from an HSPG receptor binding region of apolipoprotein B, or a variant or truncation thereof. Hence, in a third aspect, there is provided use of a polypeptide, or a derivative or analogue thereof, comprising repeats of a peptide derived from an HSPG receptor binding region of apolipoprotein B, for the, manufacture of a medicament for the treatment of a fungal and/or protist infection, or contamination.

Preferably, the polypeptide, derivative or analogue thereof comprises a repeat which is derived from an apolipoprotein B LDL receptor binding domain cluster B. Preferably, the polypeptide, derivative or analogue thereof comprises a repeat of the peptide $apoB_{3359-3367}$ (SEQ ID No. 6) or a truncation or variant thereof.

The polypeptide according to the third aspect of the invention may be a tandem dimer repeat of $apoB_{3359-3367}$ (SEQ ID No. 6) with the amino acid sequence: RLTRKRGLKRLTRKRGLK, i.e. an 18-mer (SEQ ID No.36).

Peptides according to the third aspect of the invention may also be truncated as defined herein. The reduction of amino acids may be by removal of residues from the C- and/or N-terminal, or may be by deletion of one or more amino acids from within the core of the peptide (i.e. amino acids 2-17 of SEQ ID No.36).

It is preferred that polypeptides according to the third aspect comprise at least two RKR motifs, or more if the polypeptide is a trimer, or tetramer, and so on.

Preferred polypeptides according to the third aspect comprises the tandem dimer repeat of the peptide $apoB_{3359-3367}$ (i.e the polypeptide of SEQ ID No. 36) or a truncation thereof, characterised in that at least one amino acid residue, other than the RKR motifs, has been replaced by a Glycine (G), Threonine (T), Histidine (H), Tryptophan (W), Arginine (R) or Leucine (L) residue or derivatives thereof.

Suitably, one or more, more suitably, two or more, and even more suitably, three or more amino acid residues may be replaced by a Glycine (G), Threonine (T), Histidine (H), Tryptophan (W), Arginine (R) or Leucine (L) residue or derivative thereof. Preferably, four or more, more preferably, five or more, and even more preferably, six or more amino acid residues may be replaced by these amino acids or derivative thereof. Preferably, the replaced or substituted residue is the first, second, third, seventh, eighth, ninth, tenth, eleventh, twelfth; sixteenth, seventeenth or eighteenth residue of SEQ ID No.36.

Preferably, the polypeptide according to the third aspect comprises the polypeptide of SEQ ID No.36 or a truncation thereof, characterised in that at least one amino acid residue has been replaced by a Tryptophan (W), Arginine (R) or Leucine (L) residue or derivative thereof.

Suitably, one or more, more suitably, two or more, and even more suitably, three or more amino acid residues may be replaced by a Tryptophan (W), Arginine (R) or Leucine (L) residue or derivative thereof. Preferably, four or more, more preferably, five or more, and even more preferably, six or more amino acid residues may be replaced by a Tryptophan (W), Arginine (R) or Leucine (L) residue or derivative thereof. Preferably, the replaced or substituted residue is the first, second, third, seventh, eighth, and/or ninth residue of the repeated amino acid sequence of $apoB_{3359-3367}$, or combinations thereof.

The polypeptide according to the invention may comprise 18 amino acids (or derivatives thereof) and thereby correspond to the full length of SEQ ID No.36 with or without the substitutions discussed above. However, the inventors have surprisingly found that, truncated polypeptides based on SEQ ID No.36 also have efficacy as antifungal and/or antiprotist agents. Accordingly, preferred polypeptides or derivatives thereof may have less than 18 amino acids. For instance, some polypeptides according to the third aspect of the invention may be 17, 16, 15, 14, 13, 12, 11, 10 or less amino acids in length. Deletions are preferably made at positions 1, 2, 8, 9, 10, 11, 17 and/or 18 of SEQ ID No.36.

In a preferred embodiment, the polypeptide according to the third aspect may preferably have formula IV:

{abcRKRxyz}+{a'b'c'RKRx'y'z'} wherein a & a'=is independently selected from a positively charged residue, which may be selected from either Arginine (R) or Lysine (K) or Histidine (H); Leucine (L); Tryptophan (W); or is deleted;

b & b'=is independently selected from Leucine (L); Arginine (R); Lysine (K); or is deleted;

c & c'=is independently selected from Threonine (T); Tryptophan (W); or a positively charged residue, which may be selected from Arginine (R) or Lysine (K) or Histidine (H);

x & x'=is independently selected from Glycine (G); Tryptophan (W); Leucine (L); or a positively charged residue, which may be selected from Arginine (R) or Lysine (K) or Histidine (H);

y & y'=is independently selected from Leucine (L); a positively charged residue, which may be selected from Arginine (R) or Lysine (K) or Histidine (H); or is deleted;

z & z'=is independently selected from a positively charged residue, which may be selected from Arginine (R) or Lysine (K) or Histidine (H); or Leucine; or is deleted.

The polypeptide according to the third aspect may also preferably have formula V:

{abcRKRxyz}+{abcRKRxyz} wherein a=is independently selected from a positively charged residue, which may be selected from either Arginine (R) or Lysine (K) or Histidine (H); Leucine (L); Tryptophan (W); or is deleted;

b=is independently selected from Leucine (L); Arginine (R); Lysine (K); or is deleted;

c=is independently selected from Threonine (T); Tryptophan (W); or a positively charged residue, which may be selected from Arginine (R) or Lysine (K) or Histidine (H);

x=is independently selected from Glycine (G); Tryptophan (W); Leucine (L); or a positively charged residue, which may be selected from Arginine (R) or Lysine (K) or Histidine (H);

y=is independently selected from Leucine (L); a positively charged residue, which may be selected from Arginine (R) or Lysine (K) or Histidine (H); or is deleted;

z=is independently selected from a positively charged residue, which may be selected from Arginine (R) or Lysine (K) or Histidine (H); or Leucine (L); or is deleted.

The polypeptide of formula V may more preferably comprise the following amino acids:

a=is independently selected from Tryptophan (W); Arginine (R); Leucine (L); or is deleted;

b=is independently selected from Leucine (L); Arginine (R) or Lysine (K); or is deleted;

c=is independently selected from Tryptophan (W); Threonine (T); Lysine (K);

x=is independently selected from Tryptophan (W); Glycine (G); Leucine (L); Arginine (R);

y=is independently selected from Leucine (L); a positively charged residue, which may be selected from Arginine (R) or Lysine (K) or Histidine (H); or is truncated here;

z=is independently, selected from a positively charged residue, which may be selected from Arginine (R) or Lysine (K) or Histidine (H); or Leucine (L); or is truncated here.

The inventors have also appreciated that polypeptides may be employed according to the invention that comprise more than just a tandem dimer repeat of $apoB_{3359-3336}$ (SEQ ID No.36) or a variant or truncation thereof. For example, polypeptides comprising a trimer, or tetramer, or even greater number of repeats of SEQ ID No.6 may be employed as useful antifungal/protist agents.

Accordingly, it is preferred that the polypeptide may preferably have formula VI:—

$$\{abcRKRxyz\}^n$$

wherein a, b, c, x, y, and z are as defined above with reference to formula IV or V, and wherein n is equal to 2, 3, 4 or 5, or more. It will be appreciated that monomer peptides {abcRKRxyz} may be identical or may vary as defined above.

Other preferred polypeptides may comprise repeats of the 18mer (or truncations thereof) defined by formula IV or V (e.g. repeats of a heterodimer of the 9mer peptides defined by formula IV).

Other preferred polypeptides according to the third aspect of the invention may comprise one of the following amino acid sequences:

a) RTRKRGRRTRKRGR (SEQ ID No.37). This polypeptide is designated GIN 36 when referred to herein;
b) LRKRKRLLRKRKRL (SEQ ID No.38). This polypeptide is designated GIN 37 when referred to herein;
c) LRKRKRLRKLRKRKRLRK (SEQ ID No.39). This polypeptide is designated GIN 38 when referred to herein;
d) WRWRKRWRKWRWRKRWRK (SEQ ID No.40). This polypeptide is designated GIN 33 when referred to herein;
e) LLRKRLKRLLLRKRLKRL (SEQ ID NO.41). This polypeptide is designated MU 24 when referred to herein;
f) RRWRKRWRKWRWRKRWRK (SEQ ID NO.42). This polypeptide is designated. MU 28 when referred to herein;
g) KRWRKRWRKWRWRKRWRK (SEQ ID NO.43). This polypeptide is designated MU 29 when referred to herein;
h) LRWRKRWRKWRWRKRWRK (SEQ ID NO.44). This polypeptide is designated MU 30 when referred to herein;
i) HRWRKRWRKWRWRKRWRK (SEQ ID NO.45). This polypeptide is designated MU 31 when referred to herein;
j) RWRKRWRKWRWRKRWRK (SEQ ID NO.46). This polypeptide is designated MU 32 when referred to herein;
k) RRWRKRWRKRRWRKRWRK (SEQ ID NO.47). This polypeptide is designated MU 33 when referred to herein;
l) LRWRKRWRKLRWRKRWRK (SEQ ID NO.48). This polypeptide is designated MU 35 when referred to herein;
m) HRWRKRWRKHRWRKRWRK (SEQ ID NO.49). This polypeptide is designated MU 36 when referred to herein;
n) RWRKRWRKRWRKRWRK (SEQ ID NO.50). This polypeptide is designated MU 37 when referred to herein;
o) RWRKRGRKRWRKRGRK (SEQ ID NO.51). This polypeptide is designated MU 69 when referred to herein;
p) RWRKRWRKRWRKRWRK (SEQ ID NO.52). This polypeptide is designated MU 71 when referred to herein;
q) RKRGWKWRKRGWKW (SEQ ID NO.53). This polypeptide is designated MU 73 when referred to herein;
r) RLTRKRGRLTRKRG (SEQ ID NO.54). This polypeptide is designated MU 74 when referred to herein; and
s) WRWRKRWRKWRWRKRWRK (SEQ ID NO.55). This polypeptide is designated MU 27 when referred to herein;

Derivatives of polypeptides according to the invention may be used to treat fungal and/or protist infections. Such derivatives may increase or decrease the polypeptide's half-life in vivo. Examples of derivatives capable of increasing the half-life of polypeptides according to the invention include peptoid derivatives of the polypeptides, D-amino acid derivatives of the polypeptides, and peptide-peptoid hybrids.

Polypeptides according to the invention may be subject to degradation by a number of means (such as protease activity in biological systems). Such degradation may limit the bioavailability of the polypeptides and hence the ability of the polypeptides to achieve their biological function. There are wide ranges of well-established techniques by which derivatives that have enhanced stability in biological contexts can be designed and produced. Such polypeptide derivatives may have improved bioavailability as a result of increased resistance to protease-mediated degradation. Preferably, a derivative or analogue suitable for use according to the invention is more protease-resistant than the peptide from which it is derived.

Preferably, the polypeptide may be made more protease-resistant by protecting the N and/or C terminal. For example, the N terminal may be protected by an acetyl group, or by an alkyl or aryl group, or an alkyl-CO— or aryl-CO— group, each of which may be optionally substituted. The C terminal may be protected by an amide group or by a substituted amide group.

Protease-resistance of a polypeptide derivative and the polypeptide from which it is derived may be evaluated by means of well-known protein degradation assays. The relative values of protease resistance for the polypeptide derivative and polypeptide may then be compared.

Peptoid derivatives of the polypeptides of the invention may be readily designed from knowledge of the structure of the polypeptide according to the first, second or third aspect of the invention. Commercially available software may be used to develop peptoid derivatives according to well-established protocols.

Retropeptoids, (in which all amino acids are replaced by peptoid residues in reversed order) are also able to mimic antibacterial polypeptides derived from apolipoproteins. A retropeptoid, is expected to bind in the opposite direction in the ligand-binding groove, as compared to a peptide or peptoid-peptide hybrid containing one peptoid residue. As a result, the side chains of the peptoid residues are able to point in the same direction as the side chains in the original peptide.

A further embodiment of a modified form of polypeptide according to the invention comprises D-amino acid forms of the polypeptide. The preparation of peptides using D-amino acids rather than L-amino acids greatly decreases any unwanted breakdown of such an agent by normal metabolic processes, decreasing the amounts of agent which need to be administered, along with the frequency of its administration.

Other modifications in polypeptide sequences are also envisaged and within the scope of the claimed invention, i.e. those which occur during or after translation, e.g. by acetylation, amidation, carboxylation, phosphorylation, proteolytic cleavage or linkage to a ligand.

The inventor believes that polypeptides, derivatives or analogues according to the invention may be used in the prevention or treatment of any fungal or protist infection. According to one preferred embodiment of the invention medically important species (e.g. animals and man) may be treated according to the first second or third aspects of the invention to prevent or treat an infection cause by a fungus. By the term "fungus", we mean any of the numerous eukaryotic organisms of the kingdom Fungi. These tend to lack chlorophyll, and may range in form from single cellular to multicellular, and may be branched filamentous hyphae that often produce fruiting bodies. Hence, the fungus may be filamentous.

Examples of fungal species, which cause medically important fungal infections (for example in man or in veterinary situations), and which may be treated by the peptides according to the invention may be independently selected from a group consisting of: Chytridiomycota; Zygomycota; Ascomycota; Basidiomycota; Lichens; Deuteromycota; Mitosporidia; and Straminipila.

Preferred Chytridiomycota against which the peptides according to the invention may have activity may be independently selected from a group consisting of: Neocallimasticales; Blastocladiales; Chytriddiales; Spizellomycetales; and Monoblepharidales.

Preferred Zygomycota against which the peptides according to the invention may have activity may be independently selected from: Mucorales; or Entomophthorales.

Preferred Basidiomycota against which the peptides are active may be independently selected from a group consisting of: Sporidiales, and Hymenomycetes. Preferred, sporidiales may include *Cryptococcus neoformans*, and preferred Hymenomycetes may include *Malassezia* spp.

Preferred Mucorales against which the peptides according to the invention are active may be independently selected from a group consisting of: Mucoraceae; Absidia; Apophysomyces; Mucor; Rhizomucor; Syncephalastraceae; Mortierellaceae; Saksenaeaceae; Thamnidiaceae; and Cunninghamellaceae.

Preferred Mucoraceae against which the peptides are active may include *Rhizopus*, for example, *Rhizopus arrhizus*. Preferred Absidia include *Absidia corymbifera*. Preferred Apophysomyces include *Apophysomyces elegans*. Preferred Syncephalastraceae include *Syncephalastrum racemosum*. Preferred Saksenaeaceae include *Saksenaea vasiformis*. Preferred Thamnidiaceae include *Cokeromyces recurvatus*. Preferred Cunninghamellaceae include *Cunninghamella bertholletiae*.

Preferred Entomophthorales against which the peptides according to the invention are active may be independently selected from a group consisting of: Basidiobolaceae; Entomophthoraceae; Completoriaceae; Ancylistaceae; Meristacraceae; and Neozygitaceae. Preferred Basidiobolaceae include *Basidiobolus ranarum* and *Lacazia loboi*. Preferred Ancylistaceae include *Conidiobolus coronatus* and *Conidiobolus incongruus*.

Preferred Ascomycota against which the peptides are active may be independently selected from a group consisting of: Ascomycetes and Endomyetes.

Preferred Ascomycetes against which the peptides according to the invention are active may be independently selected from a group consisting of: Onygenales; *Histoplasma* spp.; Onygenaceae; Laboulbeniomycetes; Protoascomycetes; Euascomycetes; Chaetothyriales; Ascomycotina; Paracoccidioides; *Cladosporium*; Endomycetes; Saccharomycetales; Dipodascaceae; and Saccharomycetaceae.

Preferred Onygenales include Arthrodermataceae, for example, *Epidermophyton* spp.; *Microsporum* spp. and *Trichophyton* spp. Preferred *Histoplasma* spp. include *Histoplasma capsulatum*. Preferred Euascomycetes may be independently selected from a group consisting of *Bipolaris* spp, *Blastomyces dermatitidis, Coccidioides immitis, Coccidioides posadasii, Curvularia* spp., *Fonsecaea, Leptosphaeria* spp., *Madurella, Neotestudina* spp., *Phialophora, Piedraia* spp., *Pseudallescheriam, Pyrenochaeta, Scedosporium* spp., *Scopulariopsis* spp. and *Sporothrix schenckii*. Preferred Chaetothyriales include *Exophiala* spp. and *Wangiella* spp. Preferred Ascomycotina include *Acremonium* spp. Preferred Paracoccidioides include *Paracoccidioides brasiliensis*. Preferred Endomycetes include *Saccharomycetales*, including Dipodascaceae and Saccharomycetaceae. Preferred Dipodascaceae include *Dipodascus* and *arthroconidia*.

Most preferred Saccharomycetaceae against which the peptides according to the invention are active may be independently selected from a group consisting of: *Candida*; Eurotiales; and Hypocreales.

Examples of preferred *Candida* spp against which the peptides according to the invention may be active may be independently selected from a group consisting of: *Candida tropicalis; Candida glabrata; Candida parapsilosis; Candida krusei; Candida lusitaniae*; and most preferably, *Candida albicans*. A most preferred *Candida albicans* is *Candida albicans* 6862.

Preferred Eurotiales include *Aspergillus* spp. Preferred *Aspergillus* against which the peptides according to the invention may be active may be independently selected from a group consisting of: *Aspergillus flavus; Aspergillus fumigatus; Aspergillus glaucus; Aspergillus nidulans; Aspergillus niger*; and *Aspergillus terreus*. A most preferred *A. fumigatus* is AF293.

Preferred Hypocreales include *Fusarium* spp. Preferred *Fusarium* against which the peptides according to the invention may be active may be independently selected from a group consisting of: *Fusarium solani; Fusarium oxysporum*; and *Fusarium chlamydosporum*. Most preferred *Fusarium* spp include either *Fusarium* spp 5889 or *Fusarium* spp 6507.

Polypeptides, derivatives or analogues according to the invention may be used in the treatment against any protist, or protist infection, or contamination therewith. By the term "protist", we mean any of the numerous generally unicellular eukaryotic organisms of the kingdom Protista. However, it will be appreciated that some protists are multicellular. The protist may be a protozoan. Some forms of Protista are responsible for causing disease, especially in humans.

For example, preferred protists (or Protocista) against which the peptides in accordance with the present invention are effective may be independently selected from a group consisting of: Chlorophyta (Green Algae); Phaeophyta (Brown Algae); Pyrrophyta (Dinoflagellates); Chrysophyta (Diatoms); Rhodophyta (Red Algae); Charophyta (Stoneworts); and Euglenophyta (Euglena).

Further examples of preferred protists include organisms within the Phylum Apicomplexa, such as, organisms independently selected from a group consisting of: *Coccidia; Hemogregarina* spp.; *Eimeria; Isospora; Sarcocystis cruzi; Toxoplasma* spp.; *Cryptosporidium* spp.; and *Cyclospora cayetanensis*.

Further preferred examples include Haemosporoina. Most preferred Haemosporoina include *Plasmodium* spp. It will be appreciated that *Plasmodium* spp is the protist responsible for carrying and transmitting malaria, a disease, which causes millions of deaths annually. Preferred *Plasmodium* spp may be independently selected from a group consisting of *Plasmodium vivax; Plasmodium malariae; Plasmodium ovale*; and most preferably, *Plasmodium falciparum*.

Preferred *Isospora* include *Isospora belli*. Preferred *Toxoplasma* spp. include *Toxoplasma gondii*. Preferred *Cryptosporidium* spp. include *Cryptosporidium parvum*.

Further preferred examples of protists against which the peptides in accordance with the present invention are effective may include organisms within the *Phylum myxozoa*, for example, *Myxobolus cerebralis*.

Further preferred examples of protists against which the peptides in accordance with the present invention are effective may include organisms within the Phylum Ciliophora. Preferred Ciliophora against which the peptides in accordance with the present invention are effective may be independently selected from a group consisting of: *Ichthyophthirius multifiliis*; and *Trichodina* sp. and those within the Class Litostomatea, including *Balantidium coli*.

Further preferred examples of protists against which the peptides in accordance with the present invention are effective may include organisms within the Phylum Sarcomastigophora. These organisms may include: (i) those within the subphylum Mastigophora (the flagellates); and (ii) those within the subphylum Sarcodina.

Preferred examples of organisms within the subphylum Mastigophora may be independently selected from a group consisting of *Chilomastix mesnili; Dientamoeba fragilis; Trichomonas vaginalis; Giardia lamblia; Cryptobia salmositica; Leishmania* spp; and *Trypanosoma* spp, for example, *Trypanosoma cruzi*.

Preferred examples of organisms within the subphylum Sarcodina may be independently selected from a group consisting of: *Entamoeba histolytica*; and free-living amoeba, for example, *Naegleris Fowleri, Balamuthia mandrillaris*, and *Acanthamoeba* spp. Preferred *Acanthamoeba* spp against which the peptides in accordance with the present invention are effective may include organisms may be independently selected from a group consisting of: *A. astronyxis; A. comandoni; A. divionensis; A. griffini; A. hatchetti; A. healyi; A. jacobsi; A. lenticulata; A. culbertsoni; A. lugdunensis; A. mauritaniensis; A. palestinensis; A. pearcei; A. polyphaga; A. pustulosa; A. quina; A. rhysodes; A. royreba; A. terricola; A. triangularis; A. tubiashi; A. polyphaga*; and *A. castellanii*.

The inventor conducted experiments (Example 1) to determine antifungal activity against the test fungi *Aspergillus fumigatus* AF293, *Aspergillus niger, Aspergillus terreus, Candida albicans* 6862, *Fusarium* spp 5889, and *Fusarium* spp 6507. The antifungal activity of polypeptides in accordance with the invention can be seen in Table 2. Hence, preferably, the polypeptides according to the invention exhibit antifungal activity against at least one, preferably at least two, and more preferably, all of *Aspergillus* spp. *Candida* spp., and *Fusarium* spp. Preferably, the polypeptides according to the invention exhibit antifungal activity against all of *Aspergillus, Candida albicans* 6862, *Fusarium* spp 5889, and *Fusarium* spp 6507.

The inventors have found that MU4, MU10, and MU114 are particularly active against *Aspergillus* spp, in particular, *A. fumigatus*. AF293, *Aspergillus niger*, and *Aspergillus terreus*. In addition, the inventors have found that MU4, MU10, and MU114 are particularly effective against *Candida* spp., and in particular, *Candida albicans*. Furthermore, the inventors found that MU4, MU10, and MU114 are particularly effective against *Fusarium* spp., and in particular, *F. graminarium*.

In addition to testing the activity of polypeptides disclosed herein to kill fungi, the inventor also conducted experiments (Example 2) to determine antiprotist activity against the test protists, i.e. *Acanthamoeba polyphaga* (trophozoites). As can be seen in Table 3, all three peptides in accordance with the invention (MU4, MU7, MU10, and MU114 under test) were reactive against *Acanthamoeba*, and in particular, *Acanthamoeba polyphaga*.

Further preferred antifungal and anti-protist applications are described in Examples 4 and 5 respectively.

Polypeptides according to the invention may be used to treat fungal and/or protist infections as a monotherapy (i.e. use of the polypeptide as the only anti-microbial) or in combination with other compounds or treatments used in antifungal or antiprotist therapy. For example, the polypeptides may be combined with conventional antifungal agents such as: Amorolfine, Butenafine, Naftifine, Terbinafine, Flucytosine, Fluconazole, Butoconazole, Itraconazole, Ketoconazole, Posaconazole, Ravuconazole, Voriconazole, Clotrimazole, Econazole, Miconazole, Oxiconazole, Sulconazole, Terconazole, Tioconazole, Nikkomycin Z, Caspofungin, Micafungin (FK463), Anidulafungin (LY303366), Amphotericin B (AmB), AmB Lipid Complex, AmB Colloidal Dispersion, Liposomal AmB, AmB Oral Suspension, Liposomal Nystatin, Topical Nystatin, Pimaricin, Griseofulvin, Ciclopiroxolamine, Haloprogin, Tolnaftate, Undecylenate.

Alternatively the polypeptides may be combined with conventional antiprotist agents such as: propamidine isethionate, broline, imidazoles (e.g. miconazole), topical aminoglycosides (e.g. neomycin), and topical antiseptics (e.g. polyhexamethylene biguanide), chlorhexidine propamidine, Chloroquine, Fansidar (Pyrimethamine, Sulfadoxine) Amodiaquine Quinine/Quinidine, Halofantrine, Mefloquine, Artemether/Artesunate, Malarone, Chloroquine, Proguanil, and Doxycycline.

Polypeptides according to the invention may be formulated in compositions having a number of different forms depending, in particular, on the manner in which the polypeptide is to be used. Thus, for example, the composition may be in the form of a powder, tablet, capsule, liquid, ointment, cream, gel, hydrogel, aerosol, spray, micelle, transdermal patch, liposome or any other suitable form that may be administered to a person or animal. It will be appreciated that the vehicle of the composition of the invention should be one which is well tolerated by the subject to whom it is given, and preferably enables delivery of the polypeptides or derivatives to a target tissue.

Compositions comprising polypeptides, agents, nucleic acids or derivatives according to the invention may be used in a number of ways. For instance, oral administration may be required in which case the compound may be contained within a composition that may, for example, be ingested orally in the form of a tablet, capsule or liquid. Alternatively, the composition may be administered systemically by injection into the blood stream. Injections may be intravenous (bolus or infusion) or subcutaneous (bolus or infusion). The compounds may be administered by inhalation (e.g. intranasally).

Compositions comprising polypeptides according to the invention may be orally administered or systemically administered. Furthermore, compositions may be administered by aerosol, for example, using an atomiser, which may be administered nasally, or by an inhaler via the lungs. Alternatively, the compositions may be topically applied, for example, in the form of a cream or gel. Topical administration is useful when a subject to be treated has a bacterial skin infection. The composition may be applied intravaginally (for example, if required to protect the subject from sexually transmitted diseases), or rectally.

The polypeptides and derivatives thereof may also be incorporated within a slow or delayed release device. Such devices may, for example, be inserted on or under the skin, and the compound may be released over weeks or even months. Such devices may be particularly advantageous when long-term treatment with a polypeptide or derivative according to the invention is required and which would normally require frequent administration (e.g. at least daily injection).

It will be appreciated that the amount of a polypeptide or derivative that is required is determined by its biological activity and bioavailability which in turn depends on the mode of administration, the physicochemical properties of the polypeptide, agent, nucleic acid or derivative employed and whether the polypeptide, agent, nucleic acid or derivative is being used as a monotherapy or in a combined therapy. The frequency of administration will also be influenced by the above-mentioned factors and particularly the half-life of the polypeptide, agent, nucleic acid or derivative within the subject being treated.

Optimal dosages to be administered may be determined by those skilled in the art, and will vary with the particular polypeptide in use, the strength of the preparation, the mode, of administration, the type of infection being treated or prevented and the advancement of the disease condition. Additional factors depending on the particular subject being treated will result in a need to adjust dosages, including subject age, weight, gender, diet, and time of administration.

A skilled person will appreciate that a knowledge of the $IC_{50}$ for the polypeptides will allow him or her to calculate the concentration of polypeptide in a particular formulation and also the amount of a polypeptide that should be administered to a subject in need of treatment. The inventor has found that polypeptides, and derivatives thereof, according to the invention preferably have an efficacy for inhibiting fungal growth such that their $IC_{50}$ value is about 75 μM or less, more preferably, about 60 μM or less, even more preferably, about 50 μM or less, and still more preferably, about 40 μM or less. However, it is preferred that the $IC_{50}$ value is about 30 μM or less, more preferably, about 20 μM or less, and most preferred about 10 μM or less. In fact, in the case of at least some of the peptides according to the invention, the inventor was most surprised to establish that. $IC_{50}$ values of about 5 μM or less, and even of about 2.5 μM or less were obtainable (e.g. MU4). The skilled technician will appreciate how $IC_{50}$ values may be calculated for fungi.

Polypeptides, and derivatives thereof, according to the invention preferably have an efficacy for inhibiting protist growth such that their $IC_{50}$ value is about 250 μM or less. It is more preferred that the $IC_{50}$ value for inhibiting growth of protists is about 100 μM or less, more preferably, about 50 μM or less, and most preferably, about 40 μM or less. As above, the skilled technician will appreciate how $IC_{50}$ values may be calculated for protists.

Known procedures, such as those conventionally employed by the pharmaceutical industry (e.g. in vivo experimentation, clinical trials, etc.), may be used to establish specific formulations of polypeptides or derivatives according to the invention and precise therapeutic regimes (such as daily doses and the frequency of administration).

Generally, a daily dose of between 0.01 μg/kg of body weight and 0.5 g/kg of body weight of polypeptides or derivatives according to the invention may be used for the prevention and/or treatment of a viral infection, depending upon which specific polypeptide, agent, nucleic acid or derivative is used. More preferably, the daily dose is between 0.01 mg/kg of body weight and 200 mg/kg of body weight, and most preferably, between approximately ling/kg and 100 mg/kg.

Daily doses may be given as a single administration (e.g. a single daily injection). Alternatively, the polypeptide or derivative thereof used may require administration twice or more times during a day. As an example, polypeptides according to the invention may be administered as two (or more depending upon the severity of the condition) daily doses of between 25 mg and 7000 mg (i.e. assuming a body weight of 70 kg). A patient receiving treatment may take a first dose upon waking and then a second dose in the evening (if on a two dose regime) or at 3 or 4 hourly intervals thereafter. Alternatively, a slow release device may be used to provide optimal doses to a patient without the need to administer repeated doses.

This invention provides a pharmaceutical composition comprising a therapeutically effective amount of a polypeptide or derivative according to the invention and optionally a pharmaceutically acceptable vehicle. In one embodiment, the amount of the polypeptide or derivative thereof is an amount from about 0.01 mg to about 800 mg. In another embodiment, the amount of the polypeptide, agent, nucleic acid or derivative is an amount from about 0.01 mg to about 500 mg. In another embodiment, the amount of the polypeptide or derivative is an amount from about 0.01 mg to about 250 mg. In another embodiment, the amount of the polypeptide or derivative is an amount from about 0.1 mg to about 60 mg. In another embodiment, the amount of the polypeptide or derivative is an amount from about 0.1 mg to about 20 mg.

This invention provides a process for making a pharmaceutical composition comprising combining a therapeutically effective amount of a polypeptide or derivative thereof according to the invention and a pharmaceutically acceptable vehicle. A "therapeutically effective amount" is any amount of a polypeptide or derivative according to the invention which, when administered to a subject provides prevention and/or treatment of a fungal and/or protist infection. A "subject" may be a vertebrate, mammal, domestic animal or human being.

A "pharmaceutically acceptable vehicle" as referred to herein is any physiological vehicle known to those of ordinary skill in the art useful in formulating pharmaceutical compositions.

In a preferred embodiment, the pharmaceutical vehicle is a liquid and the pharmaceutical composition is in the form of a solution. In another embodiment, the pharmaceutically acceptable vehicle is a solid and the composition is in the form of a powder or tablet. In a further embodiment, the pharmaceutical vehicle is a gel and the composition is in the form of a cream or the like.

A solid vehicle can include one or more substances, which may also act as flavouring agents, lubricants, solubilisers, suspending agents, fillers, glidants, compression aids, binders or tablet-disintegrating agents; it can also be an encapsulating material. In powders, the vehicle is a finely divided solid that is in admixture with the finely divided active polypeptide or derivative. In tablets, the active polypeptide or derivative is mixed with a vehicle having the necessary compression properties in suitable proportions and compacted in the shape and size desired. The powders and tablets preferably contain up to 99% of the active polypeptide or derivative. Suitable solid vehicles include, for example, calcium phosphate, magnesium stearate, talc, sugars, lactose, dextrin, starch, gelatin, cellulose, polyvinylpyrrolidine, low melting waxes and ion exchange resins.

Liquid vehicles are used in preparing solutions, suspensions, emulsions, syrups, elixirs and pressurized compositions. The active polypeptide or derivative can be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators.

Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be halogenated hydrocarbon or other pharmaceutically acceptable propellant.

Liquid pharmaceutical compositions which are sterile solutions or suspensions can be utilized by for example, intramuscular, intrathecal, epidural, intraperitoneal, intravenous and particularly subcutaneous, intracerebral or intracerebroventricular injection. The polypeptide or derivative may be prepared as a sterile solid composition that may be dissolved or suspended at the time of administration using sterile water, saline, or other appropriate sterile injectable medium. Vehicles are intended to include necessary and inert binders, suspending agents, lubricants, flavourants, sweeteners, preservatives, dyes, and coatings.

Polypeptides or derivatives according to the invention can be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like.

The polypeptides can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

The polypeptides or derivatives may be used to treat any mammal, for example, human, livestock, pets, to prevent infection from occurring.

By way of example, polypeptides or derivatives in accordance with the invention may be used to prevent *candida* infections. When this is the case the medicament may be formulated as a cream and it may be used in the form of a pessary.

By way of further example, polypeptides or derivatives in accordance with the invention may be used to prevent infections of "athlete's foot". When this is the case the medicament may be formulated as a cream and it may be applied to the affected area of the skin.

By way of further example, polypeptides or derivatives in accordance with the invention may be used to prevent or treat malaria. When used to prevent infection then it is preferred that a therapeutically effective amount of the polypeptide (e.g. about 10 mg of the polypeptide) is administered to the subject's skin in a suitable composition, for example, either by a cream, lotion or aerosol. It will be appreciated that methods exist, which aim to either prevent or treat malaria in man. One such treatment method (or regime) consists of intravenously administering the compound Quinine into a patient The loading dose is approximately 15 mg/kg quinine base in about 10 ml/kg normal saline or 5% dextrose, and is injected into the subject over a period of about 4 hours. Subsequent maintenance doses of about 8.3 mg/kg quinine base are then infused into the patient or subject over 4 hours, and every 8 hours, until an administration of oral quinine is possible. In patients who require more than 72 hours of intravenous treatment, the dose may be reduced to about 5.6 mg base per kg given every 8 hours. The inventor of the present invention believes that peptides in accordance with the invention may be used either on their own, or in conjunction with, or as a supplement to, existing malaria treatment regimes. For example, therapeutically effective amounts (e.g about 10 mg) of the peptide according to the invention may be added to the solution of quinone to be injected in to the subject. The peptide according to the invention may or may not be administered orally. However, it is preferred that the peptides are not administered orally.

In accordance with a fourth aspect of the invention, there is provided a method of preventing and/or treating a fungal and/or protist infection, comprising administering to a subject in need of such treatment a therapeutically effective amount of a polypeptide, derivative, or analogue or nucleic acid according to the invention.

The method according to the fourth aspect of the invention may employ any medicament and any use discussed in connection with the first, second and third aspects of the invention.

It will be appreciated that fungal and protist infections can also be a problem in plants important to horticulture and/or agriculture. Therefore the formulations of peptides discussed above may be adapted for application to plants. Thus according to a fifth aspect of the invention there is provided a method of preventing or treating a fungal and/or protist infection of a plants comprising applying a polypeptide as defined in the first, second or third aspects of the invention to a plant in need of such treatment.

The polypeptides as defined above may be used as antimicrobial agents for spraying on crops and the like. For instance the peptides may also be used to treat fungal infections of plant species, including fungal contamination, of cereal crops, fungal contamination of stored grain, potato blight and downy mildew of grapes.

Examples of fungal species, which cause agriculturally important fungal infections (for example in plants), and which may be treated by the peptides according to the invention may include preferred Ascomycetes, which may be independently selected from a group consisting of: *Erisyphe; Puccinia; Leptoshaeria; Thanatephorus; Pyricularia; Phytopthora; Plasmopara; Alternaria; Guignardia; Pseudocerocosporella; Venturia; Monolinia*; and *Ustilago*. In addition, further examples of agriculturally important fungi include *Botryotinia* spp; and *Cochilobus* spp; and most preferably, *Magnaporthe* spp. A preferred *Magnaporthe* spp. includes *M. grisea.*

The polypeptides may be used to treat any plant species suffering from a fungal or protist infection. A skilled person will appreciate that precise formulation and dosage for agricultural or horticultural use will depend on the peptide used, the type of plant treated, the size of plant treated and also the scale of treat required (for instance many acres or a single plant may be required to be treated). In general an amount of the polypeptide effective for treating a single potato plant is about 0.01-100 mgs. It is more preferred that about 10 mg of the polypeptide administered either directly onto the plant or to its roots in a suitable formulation, for example, either by a liquid or spray.

Polypeptides used according to the fifth aspect of the invention may be added to existing formulations used to treat plants, such as pesticides, weedkillers etc. For example, Ridomil Gold MZ may be applied to foliage of potato plants to control late blight caused by *Phytophthora infestans*. Early in the season, 1.2 Kg of Ridomil Gold MZ may be applied to the crop per acre. Preventative treatments are begun when conditions are favourable for disease (i.e preferably, before infection). Up to three applications may be made, at 14-day intervals. The inventor believes that such regimes for preventing potato blight may be supplemented and surprisingly improved by incorporating peptides according to the invention into the Ridomil Gold MZ solution.

The inventor has realised that the polypeptides according to the invention may also be put to a number of other antimicrobial uses (whether in a clinical context or otherwise). For instance, in addition to administering the polypeptides to a patient, animator plant, they may be used to coat surfaces and objects to prevent or treat fungal and/or a protist contamination.

Therefore, in a sixth aspect there is provided a method of preventing and/or treating a fungal and/or protist contamination comprising coating an object or a surface in need thereof with an amount of a polypeptide according to the first, second or third aspect of the invention, that is effective for killing or preventing growth of fungi and/or protists.

It will be appreciated that the polypeptide may be particularly useful for coating surfaces or objects that are required to be aseptic. As discussed above, many of the polypeptides have the advantage that they are antifungal, antiprotist, and in addition, also antiviral and antibacterial. Accordingly, the polypeptide will have a very broad anti-microbial effect across several kingdoms. Furthermore, as discussed in more detail below, the polypeptides are able to adhere to surfaces and are thereby effective for longer periods of time.

The polypeptides may be used to coat any object or device which is used in a biological or medical situation, such as a medical device, and for which it may be important to prevent a fungal or protist contamination that may lead to any infection in a patient. Examples of medical devices that may be coated according to the sixth aspect of the invention include lenses, contact lenses, catheters, stents, wound healing dressings, contraceptives, surgical implants and replacement joints.

The polypeptides are particularly useful for coating biomaterials and objects and devices made therefrom. Fungal or protist contamination/infection of biomaterials can be particularly problematic because the fungus or protist may use such material as a substrate for growth. Biomaterials (e.g. collagens and other biological polymers) may be used to surface artificial joints. Alternatively certain implants may substantially comprise such biomaterials.

The polypeptides may be used to coat surfaces in environments that are required to be aseptic. For instance the polypetides may be used in medical environments. The polypeptides may be used to keep hospital wards clean. They may be used to clean surfaces of equipment (e.g. operating tables) in operating theatres as well as theatre walls and floors. The inventors believe the polypeptides will be useful to improve sterility in general.

The polypeptides may be formulated into solutions for cleaning objects and surfaces. For instance, they may be a routine constituent of physiological solutions (for example as a constituent of physiological saline).

Example 3 illustrates how well polypeptides in accordance with the invention adhere to contact lenses. Hence, the peptides according to the invention are very useful as they have been shown to adhere strongly to an article or surface used in a biological scenario.

It will be appreciated that the above list of objects and surfaces to which the polypeptides according to the invention may be applied is not exhaustive. Hence, the polypeptides may be administered to any surface, which is prone to a fungal or protist contamination, for example, kitchen and bathroom surfaces and products, such as a toilet seat, or the toilet itself.

In a preferred embodiment, the polypeptides may be included in saline solution used to store contact lenses.

Preferred polypeptides according to the invention are highly positively charged. This makes them particularly suited for coating surfaces and objects to prevent growth of broad categories of fungi and protists. Example 3 and FIGS. 3 and 4, clearly illustrate how well the polypeptides in accordance with the invention adhere to a range of different surfaces, ie. glass (cover slips), glass previously coated with the biomaterial Poly(lactide-co-glycolide) (PLGA), and contact lenses.

Preferably, coating of the object or surface may be carried out by preparing an aqueous solution at an appropriate pH and temperature for the said polypeptides according to the invention. The object or surface is exposed to the said solution for sufficient time to allow immobilisation or absorption of a suitable quantity of the polypeptides to the surface thereof or to allow sufficient time to kill the fungus or protist.

In a preferred embodiment of the sixth aspect of the invention, a sufficiently concentrated solution of a polypeptide according to the invention is prepared, and contacted with the object to be coated for a suitable period of time. The skilled technician will appreciate how to make a polypeptide solution of the required concentration, as this will depend on the particular polypeptide being used and the fungus or protist to be treated, and the surface being coated. For example, the object may be inserted in the solution (e.g. comprising about 40 μM of the polypeptide) and left for about 15 minutes at about 20° C. Following exposure to the polypeptide, the object may be washed, for example, in a suitable buffer, such as, PBS. It may be required to leave the object in the wash buffer overnight. Following washing, the polypeptide has then adhered to the object, and the object, coated with the protective polypeptide, is ready for use.

According to a seventh aspect of the invention there is provided a contact lens at least partially coated with a polypeptide according to the first, second or third aspects of the invention. The polypeptide applied to the surface of the contact lens prevents fungal and/or protist contamination occurring that can results in infections occurring in the eye of the user.

In one embodiment, the lens may be a one day disposable lens (i.e. worn for one day and then disposed of), in which case, fungal or protist contamination is obviated before the lens is used and also when removed from its package. Accordingly, the lens my be pre-treated with the polypeptide and/or may be packaged in a solution containing the polypeptide. The lens coated with the polypeptide reduces the likelihood of a fungal infection in the user than may occur while the contact lens is being worn.

Alternatively, a lens may be repeatedly worn on a daily basis for several months or years, but taken out and washed and stored in solution over night. When this is the case a polypeptide coating on the lens (before first use) and/or preferably use of the polypeptides in lens wash solutions, will significantly reduce the likelihood of a fungal or protist infection of the user occurring while the lens is being worn, or the lens being contaminated while it is being stored and washed overnight.

In another embodiment, the lens may be an extended wear lens, which is constantly worn in the eye for extended periods of time, for example, more than one day, several days, a week or even a month or more. Users of such contact lenses have a high risk of developing a fungal or protist infection. Hence, in this case, the polypeptide may be used to coat the lens before it is first used. Use of such a coated lens will greatly reduce the likelihood of a fungal or protist infection occurring while the lens is being worn for such extended periods of time.

In a preferred embodiment, a contact lens is coated with a polypeptide according to the invention, and where appropriate, stored and/or washed in a solution comprising the polypeptide.

It will be appreciated that agents that increase the activity of polypeptides or derivatives or analogues according to the invention may be used to "indirectly" increase the activity of such polypeptides, derivatives or analogues. Thus, according to an eighth aspect of the invention, there is provided an agent capable of increasing the biological activity of a polypeptide, derivative or analogue according to the first, second or third aspect of the invention for use as a medicament for treating a fungal and/or protist infection.

Agents capable of increasing the biological activity of polypeptides, derivatives or analogues according to the invention may achieve their effect by a number of means. For instance, such agents may increase the expression of such polypeptides, derivatives or analogues. Alternatively (or in addition), such agents may increase the half-life of polypeptides, derivatives or analogues according to the invention in a biological system, for example, by decreasing turnover of the polypeptides, derivatives or analogues.

The inventor has further established that several polypeptides or agents according to the invention may be combined and used to prevent or treat a broad range of fungal or protist infections/contaminations (as well as viral and bacterial infections/contaminations). For example, it may be preferred to treat a fungal or protist infection/contamination with a combination of polypeptides according to any one of the first, second, or third aspects, such as a polypeptide independently selected from a group consisting of MU4, MU7, MU10 or MU114. However, it will be appreciated that different combinations of polypeptides can be used to prevent or treat different fungal or protist infections.

Furthermore, the polypeptide and agents according to the invention may be used to minimise, prevent or treat fungal or protist contamination or growth, by use as, or in conjunction with, a preservative. Hence, the polypeptides and agents may be used as a preservative in foodstuffs. In addition, the polypeptides and agents may be used to minimise or prevent fungal or protist growth in cultures, for example, in tissue culture work, either to supplement, or to replace antibiotics and other antifungal/antiprotist agents. In addition, the polypeptides may be used as selective agents as a diagnostic agent, for example, for fungal or protist growth in culture media. For example, a first polypeptide may be added to media, which is particularly active against a first fungus, and a second polypeptide may be added to the media, which is particularly active against a second fungus. A similar method could be used for diagnosing protista.

The polypeptides, analogues, or derivatives of the invention represent products that may advantageously be expressed by biological cells. Therefore the present invention also provides, in a ninth aspect, a nucleic acid sequence encoding a polypeptide, derivative or analogue according to the first, second or third aspects of the invention.

Preferred nucleic acids according to the ninth aspect of the invention may be selected from the group consisting of: SEQ ID No.56 (cttcgtaaacttcgtaaacgtcttctt), SEQ ID No.57 (cgtcttactc gtaaacgtggtcttaaa), SEQ ID No.58 (cttcgtaaacgtcttcttctcgtaaacttcgtaaacgtcttctt), SEQ ID No.59 (caatctactgaagaacttcgtgttcgtcttgctagtcatcttcgtaaacttcgtaaacgtcttctt), SEQ ID No.60 (cttcgtgttcgtcttgctagtcatcttcgtaaacttcgtaaacgtcttcttcgtgatgctgatgatcttcaaaaacgtct tgctgtttatcttcgtgttcgtcttgctagtcatcttcgtaaacttcgtaaacgtcttcttcgtgatgctgatgatcttcaaaaacgtc ttgctgtttat), SEQ ID No.61 (cttcgtaaacttcgtaaacgtcttcttcttcgtaaacttcgtaaacgtcttctt), SEQ ID No.62 (tggcgtaaatggcgtaaacgttggtggtggcgtaaatggcgtaaacgttggtgg), SEQ ID No.63 (tggcgtaaatggcgtaaacgttggtggcgtaaatggcgtaaacgttgg), SEQ ID No.64 (tggcgtaaat ggcgtaaacgttggtggcttcgtaaacttcgtaaacgtcttctt), SEQ ID No.65 (tatcgtaaatatcgtaaacg ttattattatcgtaaatatcgtaaacgttattat), SEQ ID No.66 (cttcgtaaacttcgtaaacgtcttcgtaaacttcgtaaacgt), SEQ ID No.67 (cgtcttactcgtaaacgtgg tcttaaacgtcttactcgtaaacgtggtcttaaa), SEQ ID No.68 (cgtactcgtaaacgtggtcgtcgtactcgt aaacgtggtcgt), SEQ ID No.69 (cttcgtaaacgtaaacgtcttcttcgtaaacgtaaacgtctt), SEQ ID No.70 (cttcgtaaacgtaaacgtcttcgtaaacttcgtaaacgtaaacgtcttcgtaaa), SEQ ID No.71 (tggcgttggcgtaaacgttggcgtaaatggcgttggcgtaaacgttggcgtaaa), SEQ ID No.72 (MU4) (tggcgtaaatggcgtaaacgttggtggtggcgtaaatggcgtaaacgttggtgg), SEQ ID No.73 (MU7) (tttcgtaaatttcgtaaacgtttttttttcgtaaatttcgtaaacgtttttt), SEQ ID No.74 (MU10) (ttacgtaaattacgtaaacgtttattattacgtaaattacgtaaacgtttatta), and SEQ ID No.75 (MU114) (tggcgtaaatggcgtaaacgtttattattacgtaaattacgtaaacgtttatta).

Preferred nucleic acids further include those corresponding DNA molecules encoding any preferred polypeptides according to the invention.

It will be appreciated that, due to redundancy in the genetic code, a nucleic acid sequence in accordance with the invention may vary from the naturally occurring sequence (e.g. in the ApoB or ApoE genes) providing a codon encodes a polypeptide, derivative or analogue thereof in accordance with the first, second or third aspect of the invention.

It will be appreciated that polypeptides, derivatives and analogues according to the invention represent favourable agents to be administered by techniques involving cellular expression of nucleic acid sequences encoding such molecules. Such methods of cellular expression are particularly suitable for medical use in which the therapeutic effects of the polypeptides, derivatives and analogues are required over a prolonged period.

Thus according to a tenth aspect of the present invention there is provided a nucleic acid sequence according to the previous aspect of the invention for use as a medicament.

According to an eleventh aspect, there is provided use of the nucleic acid, for the preparation of medicament for treating a fungal anchor protist infection.

The nucleic acid may preferably be an isolated or purified nucleic acid sequence. The nucleic acid sequence may preferably be a DNA sequence.

The nucleic acid sequence may further comprise elements capable of controlling and/or enhancing its expression. The nucleic acid molecule may be contained within a suitable vector to form a recombinant vector. The vector may for example be a plasmid, cosmid or phage. Such recombinant vectors are highly useful as delivery systems for transforming cells with the nucleic acid molecule.

Recombinant vectors may also include other functional elements. For instance, recombinant vectors can be designed such that the vector will autonomously replicate in the cell. In this case elements that induce nucleic acid replication may be required in the recombinant vector. Alternatively, the recombinant vector may be designed such that the vector and recombinant nucleic acid molecule integrates into the genome of a cell. In this case nucleic acid sequences, which favour targeted integration (e.g. by homologous recombination) are desirable. Recombinant vectors may also comprise DNA coding for genes that may be used as selectable markers in the cloning process.

The recombinant vector may also further comprise a promoter or regulator to control expression of the gene as required.

The nucleic acid molecule may (but not necessarily) be one, which becomes incorporated in the DNA of cells of the subject being treated. Undifferentiated cells may be stably transformed leading to the production of genetically modified daughter cells (in which case regulation of expression in the subject may be required e.g. with specific transcription factors or gene activators). Alternatively, the delivery system may be designed to favour unstable or transient transformation of differentiated cells in the subject being treated. When this is the case, regulation of expression may be less important because expression of the DNA molecule will stop when the transformed cells die or stop expressing the protein (ideally when the required therapeutic effect has been achieved).

A delivery system may provide the nucleic acid molecule to the subject without it being incorporated in a vector. For instance, the nucleic acid molecule may be incorporated within a liposome or virus particle. Alternatively a "naked" nucleic acid molecule may be inserted into a subject's cells by a suitable means, e.g. direct endocytotic uptake.

The nucleic acid molecule may be transferred to the cells of a subject to be treated by transfection, infection, microinjection, cell fusion, protoplast fusion or ballistic bombardment. For example, transfer may be by ballistic transfection with coated gold particles, liposomes containing the nucleic acid molecule, viral vectors (e.g. adenovirus) and means of providing direct nucleic acid uptake (e.g. endocytosis) by application of the nucleic acid molecule directly.

Embodiments of the invention will now be further described, by way of example only, with reference to the following Example and figures in which.

Figure 4:
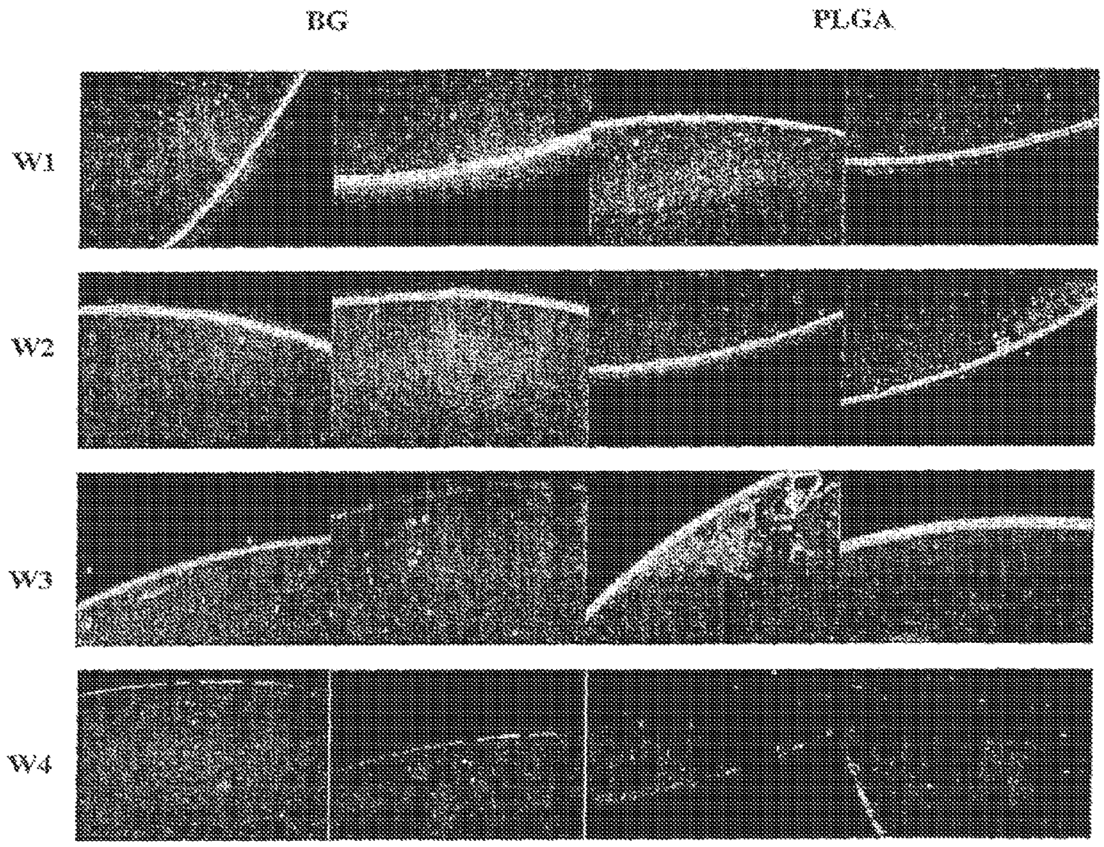

FIG. 3 illustrates Johnson and Johnson Acuvue contact lenses, which had been treated for 15 min with 40 μM GIN1p (which had been synthesised with the addition of a cysteine residue having a fluorescent tag), then washed 4 times, including an overnight soak in 25 ml PBS as discussed in Example 3;

FIG. 4 illustrates glass cover slips (BG), or cover slips previously coated with the biomaterial Poly(lactide-co-glycolide) (PLGA), which had been treated for 15 min with 40 μM GIN1p (which had been synthesised with a fluorescent tag), then washed 4 times, including an overnight soak in 25 ml PBS as discussed in Example 3; and FIG. 5 illustrates inhibition of hepatocyte invasion by *plasmodium* spp mediated by peptides according to the invention of: (A) cells incubated with *Plasmodium* and peptide; and (B) cells incubated with *Plasmodium*, washed, and then peptide added as discussed in Example 5.

EXAMPLES

The inventor carried out a number of experiments to investigate the antifungal and also antiprotist activity of polypeptides according to the invention. The activity of the polypeptides was tested against a number of different fungi (Examples 1 and 4) and protists (Example 2 and 5). In addition, the inventor investigated the ability of the polypeptides to adhere to a variety of surfaces, for example, contact lenses, glass and surfaces coated with the biomaterial "PLGA" (Example 3) and thereby prevent fungal or protist contamination.

Peptides

Peptides (including polypeptides according to the invention) were obtained in lyophilised form from a commercial supplier (AltaBioscience, University of Birmingham), and were produced at 5 micromole scale. The skilled technician will know the standard techniques, which are available for synthesising peptides, once an amino acid sequence has been made available. N-terminals were protected by addition of an acetyl group, and the C-terminals were protected by addition of an amide group. Small quantities of peptide were weighed in sterile Eppendorf tubes, before addition of sufficient PBSA to produce a 0.4 mM stock solution, which was frozen at −85° C. in aliquots.

Figure 1:
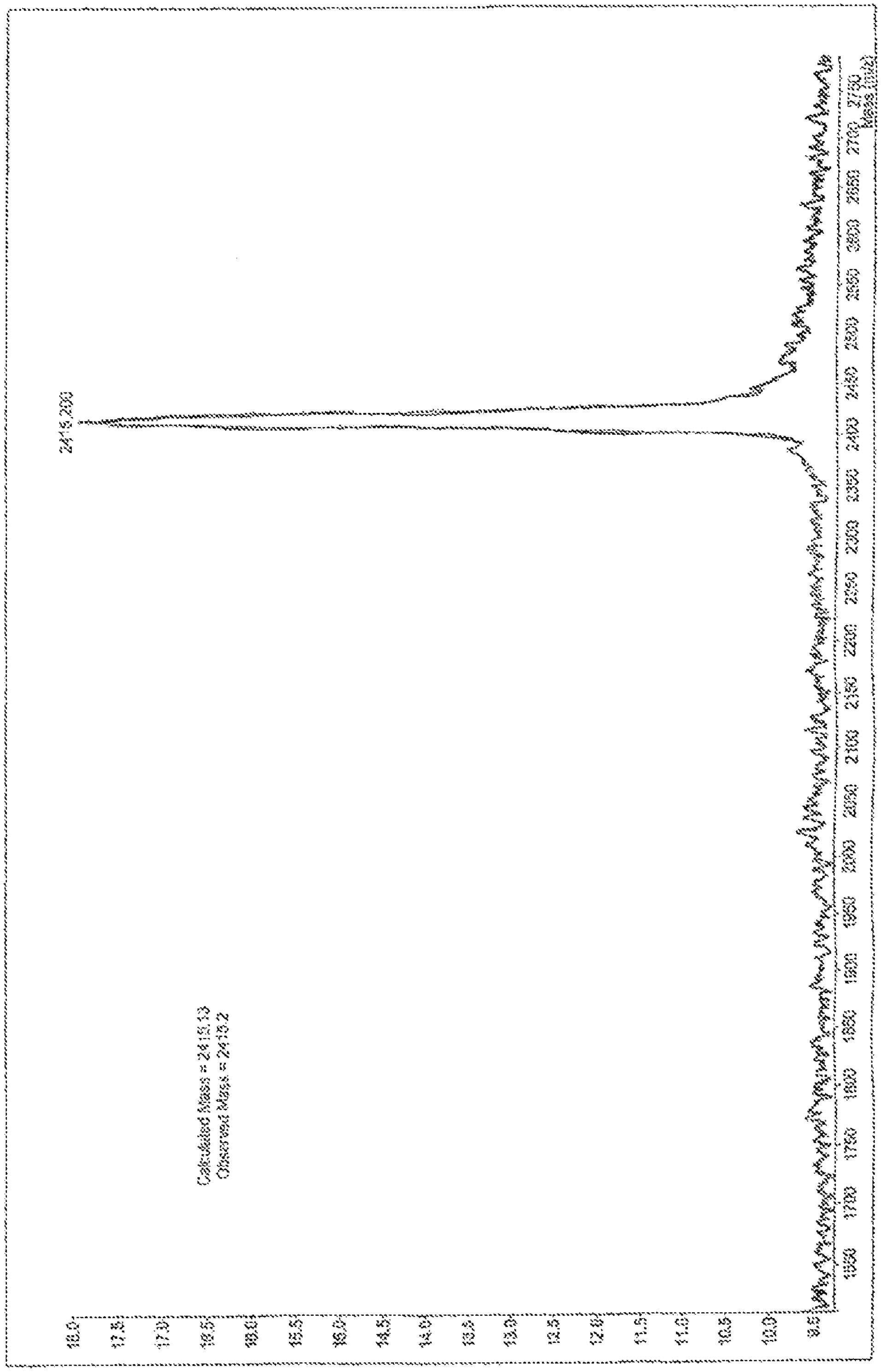
FIG. 1 shows typical mass spectrometry data and illustrates that the peptide was >95% purity.
Figure 2:
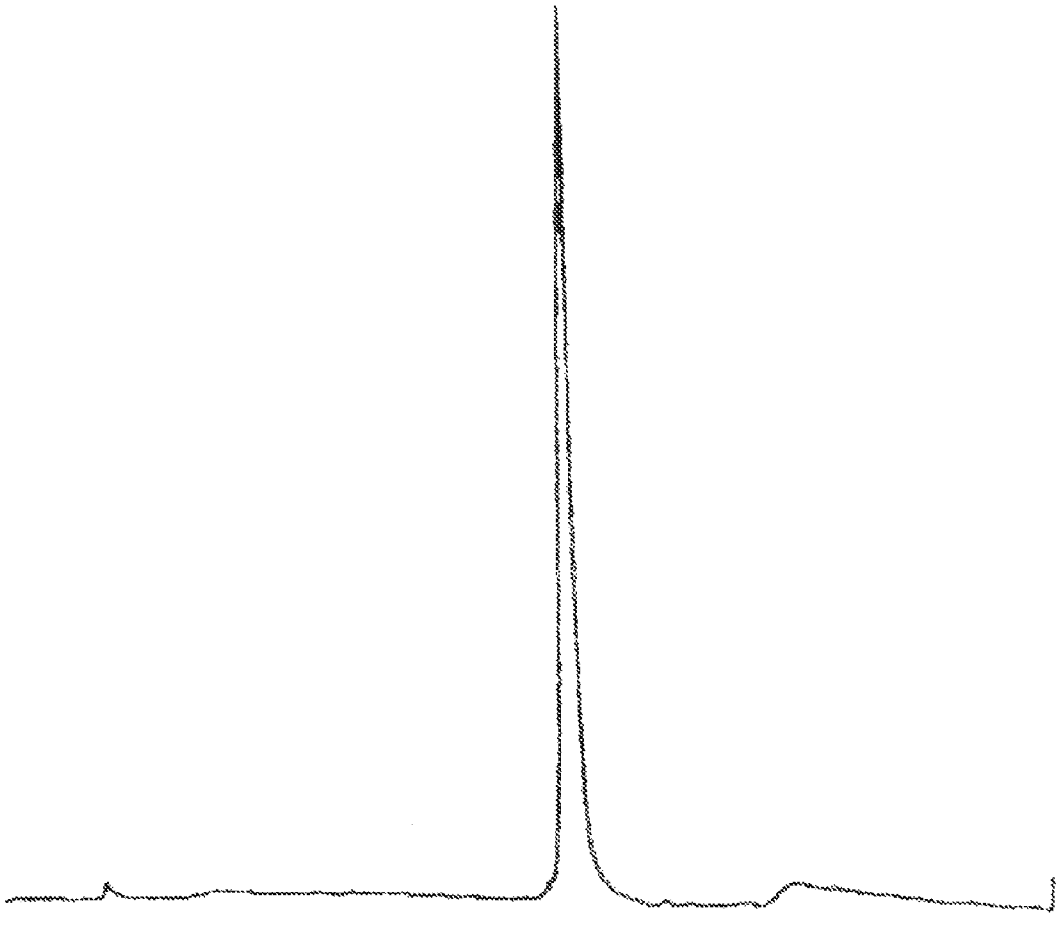
FIG. 2 shows typical HPLC data and illustrates that the peptide was >95% purity.

Molecular weight of peptides was confirmed by laser desorption mass spectrometry using a Finnigan LASERMAT 2000 MALDI-time of flight mass analyzer or a Scientific Analysis Group MALDI-TOF mass spectrometer. HPLC purification of peptides was performed using a Vydac analytical C-4 reverse phase column, using 0.1% TFA and 0.1% TFA/80% acetonitrile as solvents, or for some peptides an ACE C18 Reverse Phase column, using 0.05% TFA and 60% acetonitrile as solvents. Typical mass spectrometry data and high performance liquid chromatography (HPLC) traces (purity>95%) for peptide GIN1p are shown in FIGS. 1 and 2.

Example 1

Experiment to Test the Antifungal Activity of Peptides

Four compounds were supplied as an aqueous solution, 400 μM. Serial dilutions of each test peptide were prepared in addition to a control, which was a conventional antifungal drug, Amphoteracin B. Amphteracin B is obtained from Invitrogen or Melford laboratories.

The peptides under test were:

```
                                    (SEQ ID No. 9)
(i) MU4 - WRKWRKRWWWRKWRKRWW;

                                    (SEQ ID NO.  8)
(ii) MU10 - LRKLRKRLLLRKLRKRLL;
and

                                    (SEQ ID NO.  26)
(iii) MU114 - WRKWRKRLLLRKLRKRLL.
```

Initial testing of the peptides was carried out against the following organisms:

1) *Aspergillus fumigatus* AF293 (culture collection strain NCPF7367)
2) *Candida albicans* 6862 (clinical isolate)
3) *Fusarium* spp 5889 (clinical isolate)
4) *Fusarium* spp 6507 (clinical isolate)
5) *Aspergillus terreus* (clinical isolate)
6) *Aspergillus niger* (clinical isolate)
7) *Staphylococcus aureus* (Oxford strain, which is a standard reference strain used in MIC testing)

The bacterium *S. aureus* was tested with each of the peptides as a control. A suspension of each organism in an appropriate growth medium was added to the, dilutions of the peptides in order to give concentration ranges of 40 μM to 0.04 μM for each of the peptides, and 64-0.025 μg/ml for amphotericin B. Fungal strains were tested in RPMI media. RPMI is standard Roswell Park Memorial Institute medium (Morton, H. C., (1970) A survey of Commercially Available Tissue Culture Media. In Vitro 6: 89-108).

*S. aureus* was tested in Isosensitest broth. Isosentitest agar is a standard MIC medium used by many hospital labs for bacterial MICs using a disc diffusion method. The reference standard is Oxoid CM471. Also available in broth form, CM473, for the bacterial broth dilution assay method. NCCLS ref M7-A4. Both the NCCLS methods quoted are the standard methods.

The final inoculum for *S. aureus* was $5\times10^4$ cfu/ml. The final inoculum for *C. albicans* was $2\times10^3$ cfu/ml. The final inoculum for *Aspergillus fumigatus* and for *Fusarium* spp was $2\times10^4$ cfu/ml.

*Candida* and *S. aureus* plates were read after 24 hrs incubation and the *Aspergillus* and *Fusarium* strains read after 48 hrs. The MIC was taken as the lowest drug or compound concentration that caused >80% reduction in growth compared with a drug free control.

TABLE 2

Antifungal effect of peptides

| | Amphotericin MIC in μg/ml | MU_4 MICs in μM | MU_10 MICs in μM | MU_114 MICs in μM |
|---|---|---|---|---|
| *C. albicans* 6862 | 0.6 | 10 | >40 | >40 |
| *Aspergillus fumigatus* | 0.6 | 2.5 | >40 | >40 |
| *Fusarium* spp 5889 | 2.5 | 2.5 | 10 | 5 |
| *Fusarium* spp 6507 | 1.25 | 10 | >40 | 40 |
| *Aspergillus terreus* | 1.25 | >40 | >40 | >40 |
| *Aspergillus niger* | 0.15 | 1.25 | >40 | 20 |
| *Staph aureus* (Oxford) | >40 | 5 | >40 | 40 |

From Table 2, it will be seen that peptide MU4 is the most active of the peptides tested having activity against all four fungal species tested, and also surprisingly, against *S. aureus* (a gram positive bacterium). Peptide MU4 is also active against *Aspergillus niger*. However, MU4 shows lower activity against *Aspergillus terreus*, which is known to be resistant to various antifungal drugs.

MU10 and MU114 also showed antifungal activity, albeit to a lesser extend than MU4. However, MU10 and MU114 showed antifungal activity against *Fusarium* 5889. The activity of the peptides is surprising in that they are more active against *Fusarium* spp than against *Aspergillus* spp.

Conclusion

Using standard antifungal testing methods, the peptides according to the invention are shown to have antifungal activity. In addition, surprisingly, some antibacterial activity is also present. Peptide MU4 is particularly potent against *Aspergillus fumigatus, Aspergillus niger* and *Fusarium* spp. The other peptides (MU10 and MU114) are less active, but still show antifungal activity.

Example 2

Experiment to Test the Antiprotist Activity of Peptides

The test compounds were screened against the trophozoites of clinical isolates of *Acanthamoeba* spp. using a microtitre plate assay procedure. The organisms were *Acanthamoeba polyphaga*. (see for details on the strain and methodology used: Hughes, R. & Kilvington, S. (2001). A comparison of hydrogen peroxide contact lens disinfection systems and solutions against *Acanthamoeba polyphaga*. Antimicrob. Agents Chemother. 45: 2038-2043.) *Acanthamoeba polyphaga* Ros strain was used throughout the study. The strain was originally isolated from an unpublished case of *acanthamoeba* keratitis in the United Kingdom in 1994.

Use of the microliter plate assay enabled the determination of the minimum amoebacidal trophozoite concentration (MATC), which is the minimum amoebacidal trophozoite concentration (μg/ml)=lowest concentration killing the trophozoite challenge (1×10-4) and also the minimum inhibitory trophozoite concentration (MITC), which is the minimum inhibitory trophozoite concentration (μg/ml)=lowest concentration stopping the trophozoites from dividing or killing about 50% of population. The values may then be used to select drug concentrations for use in time-kill experiments to study the kinetics of *Acanthamoeba* killing.

The peptides under test were:

```
                                        (SEQ ID No. 9)
(i) MU4 - WRKWRKRWWWRKWRKRWW;

                                       (SEQ ID No. 15)
(ii) MU7 - FRKFRKRFFFRKFRKRFF.

                                       (SEQ ID NO.  8)
(iii) MU10 - LRKLRKRLLLRKLRKRLL;
and

                                       (SEQ ID NO.  26)
(iv) MU114 - WRKWRKRLLLRKLRKRLL.
```

TABLE 3

Antiprotist Effects of Peptides
Values in μM

| Drug | MITC | MATC |
|---|---|---|
| MU 4 | 20.8 | 41.7 |
| MU 7 | NR | 93.1 |
| MU 10 | NR | 207.1 |
| MU 114 | NR | 98.7 |

MITC = minimum inhibitory trophozoite concentration (μM)
MATC = minimum amoebacidal trophozoite concentration (μM)
NR = Not recorded as a MITC was not observed Conclusion Referring to Table 3, it can be seen that MU4 showed the greatest antiprotist activity, having the lowest MITC and MATC values by killing *Acanthamoeba polyphaga*. MU 7 and MU114 showed good activity against *Acanthamoeba polyphaga* as they showed an MATC of 93.1 and 93.8, respectively. Finally, MU10 also showed antiprotist activity with an MATC of 207.1.

Example 3

Coating of Medical Devices with Antifungal/Antiprotist Polypeptides

Polypeptides according to the invention may be used to coat medical devices prone to contamination with fungi or protists. Examples of such medical devices include lenses, catheters, stents, wound healing dressings and contraceptive devices. The polypetides may also be applied to surfaces in medical environments, including surfaces of equipment for use in operating theatres. The inventors of the invention have shown that the polypeptides according to the invention adhere to contact lenses, glass and to surfaces coated with the biomaterial "PLGA".

Coating a surface can be carried out by preparing a concentrated aqueous solution of a polypeptide (for example 200 μM) at an appropriate pH (for example pH7.4) for the specific polypeptide. A surface is then exposed to the aqueous solution at a suitable temperature (for example 37° C.) for sufficient time (for example 2 hours) to allow immobilisation or absorption of a suitable quantity of the polypeptide to the surface thereof.

To test whether the peptides according to the invention could be immobilised on a biomaterial or other surfaces, the inventors obtained a fluorescently labelled form of the GIN1p (Advanced Biomedical, Oldham, UK). A 40 μM stock solution of this labelled polypeptide was prepared in PBS, and 250 μl aliquots were inserted in to the wells of a 24-well microplate. The inventors then placed several materials into these peptide solutions, these being: (i) Johnson and Johnson Acuvue contact lenses; (ii) bare glass coverslips; or (iii) coverslips previously coated with the biomaterial Poly(lactide-co-glycolide) (PLGA: coated slides provided by Prof Jian Lu, Department of Physics, University of Manchester).

After incubation at 20° C. for 15 min in the peptide solutions, the materials were removed, and then washed by placing in 1 ml PBS. The materials were then examined by fluorescence microscopy (using an Olympus IX70 inverting microscope fitted with a Chroma 35002v2 filter set), and the results were recorded by photography. The materials were then washed two more times in 1 ml PBS, and then finally left to soak overnight at 37° C. in 25 ml PBS. The level of fluorescence was observed and recorded after each wash, again by microscopic observation and photography as described above.

Referring to FIG. 3, there are shown Johnson and Johnson Acuvue contact lenses, which had been treated for 15 min with 40 μM GIN1p (i.e. MU10), (which had been synthesised with a fluorescent tag), then washed 4 times, including an overnight soak in 25 ml PBS. FIG. 3(*a*) shows an untreated lens and a GIN1p-treated lens (after 4 washes), under illumination with white light, or GFP fluorescence, using a Olympus IX70 microscope. Hence, even after repeated washing, the lens retains a significant quantity of peptide, such that fluorescence is visible even by eye as shown in FIG. 3(*b*). The images were captured using a Canon EOS300D digital camera, using ISO1600 film setting, and with a 0.3 s exposure time for fluorescent images.

Referring to FIG. 4, there are shown glass cover slips (BG), or cover slips previously coated with the biomaterial Poly (lactide-co-glycolide) (PLGA), which had been treated for 15 min with 40 μM GIN1p (which had been synthesised with a fluorescent tag), then washed 4 times, including an overnight soak in 25 ml PBS. The level of fluorescence was observed using an Olympus IX70 microscope for samples after each wash (W1, W2, W3 and W4). Hence, it can be seen that the level of fluorescence did not decrease noticeably after any of the washes, suggesting that the polypeptide adheres firmly to a range of surfaces. The images were captured using a Canon EOS300D digital camera, with a 5 s exposure time using ISO1600 film setting.

Accordingly, FIGS. 3 and 4 show that all three types of material appeared to retain similar levels of GIN1p despite extensive washing, suggesting the polypeptide is suitable for coating various surfaces (as shown in FIG. 1*a*, and FIG. 4). In particular, the contact lenses were found to absorb significant quantities of the polypeptide (presumably due to their large surface area), such that fluorescence was clearly visible to the naked eye, even after the fourth overnight wash as shown in FIG. 3*b*.

Conclusions

From Table 2, it will be seen that the polypeptides in accordance with the present invention show antifungal activity against at least one, if not two, and if not three, of the six different fungi trains evaluated. In particular, MU 4, MU 10, and MU 114 are particularly effective. One of the most active peptides is MU 4, which is active against *C. albicans* 6862, *Aspergillus fumigatus, Fusarium* spp. 5889, *Fusarium* spp 6507, *Aspergillus terreus*, and *Aspergillus niger.*

From Table 3, it will be seen that polypeptides in accordance with the present invention also show antiprotist activity against *Acanthamoeba polyphaga*. In particular, MU 4, MU 7, MU 10, and MU 114 are particularly effective.

It is worth noting that MU 4 was surprisingly active against fungi and protists.

Each of these polypeptides in accordance with the invention are derived from a Heparan Sulphate Proteoglycan (HSPG) receptor binding region of apolipoprotein E. In addition, each polypeptide is a tandem repeat, and comprise two RKR motifs. The data illustrates the surprising property that tandem repeats in accordance with the invention are effective antifungal and antiprotist agents.

Example 4

Antifungal Efficacy Against a Number of Fungi

The inventor expanded the work conducted in Example 1 by testing an expanded library of peptides derived from either apolipoprotein B or apolipoprotein E in order to further evaluate polypeptides in accordance with the invention. These experiments were conducted using the following fungal species:

*Fusarium solani* 1 (FS1);

*Fusarium solani* 2 (FS2);

*Fusarium solani* 3 (FS3);

*Fusarium solani* 4 (FS4);

*Aspergillus fumigatus* 293 (AF); and

*Candida albicans* (CA).

FS1-FS4 were obtained from Bristol PHLS (British Public Health Laboratory Service UK). *Aspergillus fumigatus* 293 is publicly available as culture collection strain NCPF7367 (National Collection of Pathogenic Fungi Public Health Laboratory, Mycological Reference Laboratory Myrtle Road, Kingsdown, Bristol BS2 8EL) The *Candida albicans* was a clinical isolate obtained by standard means.

The methods used to determine, the $IC_{50}$ values for each peptide were as described in the Example 1. An $IC_{50}$ of less or about 40 μM was taken to have good antifungal activity Table 4 provides data for peptides that are derived from apoE.

TABLE 4

MIC values (>80% reduction) against 6 fungal species of Peptides derived from apoE

| Peptide | SEQ. ID. No. | Sequence | FS1 | FS2 | FS3 | FS4 | AF | CA |
|---|---|---|---|---|---|---|---|---|
| MU_1 (GIN 6) | SEQ ID NO. 76 | ERKERKREEERKERKREE | >40 | >40 | >40 | >40 | >40 | >40 |
| MU_2 (GIN 39) | SEQ ID NO. 77 | ARKARKRAAARKARKRAA | >40 | >40 | >40 | >40 | >40 | >40 |
| MU_3 | SEQ ID NO. 78 | DRKDRKRDDDRKDRKRDD | >40 | >40 | >40 | >40 | >40 | >40 |
| MU_4 (GIN 7) | SEQ ID NO. 9 | WRKWRKRWWWRKWRKRWW | 0.3 | 0.3 | 0.3 | 0.3 | 1.25 | 2.5 |
| MU_5 (GIN 40) | SEQ ID NO. 32 | MRKMRKRMMMRKMRKRMM | 10 | 20 | 20 | 40 | >40 | >40 |
| MU_6 (GIN 41) | SEQ ID NO. 12 | YRKYRKRYYYRKYRKRYY | 10 | 5 | 5 | 20 | >40 | >40 |
| MU_7 | SEQ ID NO. 15 | FRKFRKRFFFRKFRKRFF | 5 | 2.5 | 5 | 20 | >40 | >40 |
| MU_8 | SEQ ID NO. 33 | IRKIRKRIIIRKIRKRII | 40 | 20 | 20 | 40 | >40 | >40 |
| MU_9 | SEQ ID NO. 79 | QRKQRKRQQQRKQRKRQQ | >40 | >40 | >40 | >40 | >40 | >40 |
| MU_10 (GIN 1p) | SEQ ID NO. 8 | LRKLRKRLLLRKLRKRLL | 2.5 | 5 | 2.5 | 5 | >40 | >40 |
| MU_11 | SEQ ID NO. 80 | NRKNRKRNNNRKNRKRNN | >40 | >40 | 40 | >40 | >40 | >40 |
| MU_12 | SEQ ID NO. 30 | CRKCRKRCCCRKCRKRCC | 2.5 | 5 | 10 | 5 | 40 | >40 |
| MU_13 | SEQ ID NO. 81 | SRKSRKRSSSRKSRKRSS | >40 | >40 | >40 | >40 | >40 | >40 |
| MU_14 | SEQ ID NO. 82 | VRKVRKRVVVRKVRKRVV | >40 | >40 | >40 | >40 | >40 | >40 |
| MU_15 | SEQ ID NO. 83 | TRKTRKRTTTRKTRKRTT | >40 | >40 | >40 | >40 | >40 | >40 |
| MU_16 | SEQ ID NO. 31 | RRKRRKRRRRRKRRKRRR | 1.25 | 1.25 | 1.25 | 2.5 | 40 | 10 |
| MU_17 | SEQ ID NO. 84 | GRKGRKRGGGRKGRKRGG | >40 | >40 | >40 | >40 | >40 | >40 |
| MU_18 | SEQ ID NO. 85 | KRKKRKRKKKRKKRKRKK | 2.5 | 10 | 2.5 | >40 | >40 | >40 |
| MU_19 | SEQ ID NO. 34 | HRKHRKRHHHRKHRKRHH | 20 | >40 | 40 | 10 | >40 | >40 |
| MU_20 | SEQ ID NO. 86 | PRKPRKRPPPRKPRKRPP | >40 | >40 | >40 | >40 | >40 | >40 |
| GIN 34 | SEQ ID NO. 11 | WRKWRKRWWLRKLRKRLL | 1.25 | 0.6 | 1.25 | 12.5 | 40 | 10 |
| MU_45 | SEQ ID NO. 87 | WRKWRKRWW | 40 | 40 | 40 | >40 | >40 | >40 |
| MU_82 | SEQ ID NO. 21 | LRKLRKRLLRLRKLRKRLLR | 2.5 | 2.5 | 2.5 | 10 | >40 | >40 |
| MU_112 | SEQ ID NO. 24 | LRKLRKRLLLRKLRKRWW | 2.5 | 2.5 | 2.5 | 5 | >40 | >40 |
| Amphotericin B (antifungal positive control) | | | | 0.15 | 1.25 | 0.3 | 0.15 | 0.04 |

In Table 4 it will be appreciated that MU1-MU20 correspond to tandem repeat of peptides based on $apoE_{141-149}$, (MU10) in which each L residue is substituted with another amino acid (MU1-MU9 and MU11-MU20). Polypeptides in accordance with the present invention exhibited good antifungal activity with $IC_{50}$ values<40 μM against at least four of the fungi tested. MU 4, MU 6, MU 7, MU10, MU12 MU16 and MU18 are particularly effective antifungal peptides. The most preferred peptide MU4 has activity comparable with amphotericin B. Table 4 illustrates that a range of peptides based upon substituted tandem repeats of peptides based on $apoE_{141-149}$, which fall outside the definition of the polypeptides according to the invention, are ineffective relative to peptides according to the invention.

It will be seen that the preferred polypeptide MU 4 (a tandem repeat of WRKWRKRWW) has good antifungal activity whereas the monomer on which it is based MU45 is ineffective. This illustrates that tandem repeats of $ApoE_{141-149}$ and derivatives thereof (as defined by herein) are surprisingly effective antifungal agents.

Table 5 presents data for peptides that are derived from apoB.

TABLE 5

MIC values for peptides derived from apolipoprotein B

| Peptide | SEQ. ID. No | Sequence | FS1 | FS2 | FS3 | FS4 | AF | CA |
|---|---|---|---|---|---|---|---|---|
| MU_25 | SEQ ID NO. 88 | WRWRRRWRKWRWRRRWRK | 5 | 5 | 10 | 20 | 10 | >40 |
| MU_26 | SEQ ID NO. 89 | WRWKKKWRKWRWKKKWRK | 5 | 5 | 5 | 10 | >40 | >40 |
| MU_27 (GIN 33) | SEQ ID NO. 55 | WRWRKRWRKWRWRKRWRK | 0.6 | 0.6 | 0.6 | 1.25 | 5 | 20 |
| MU_28 | SEQ ID NO. 42 | RRWRKRWRKWRWRKRWRK | 0.6 | 0.6 | 1.25 | 2.5 | 10 | >40 |
| Amphotericin B (antifungal positive control) | | | | 0.15 | 1.25 | 0.3 | 0.15 | 0.04 |

From Table 5, it will be seen that the peptides MU27 and MU28, which are peptides in accordance with the present invention, show good antifungal activity against at least five of the different fungal strains evaluated.

It will be appreciated that MU25 and MU26 have reduced activity. These peptides closely resemble peptides MU27 and MU28 according to the invention but have had the RKR motifs modified or changed.

Example 5

Antimalarial Efficacy of Peptides According to the Invention

Experiments were conducted to illustrate that peptides according to the invention are effective at preventing infection of cultured hepatocytes by *plasmodium* sporozoites and thereby demonstrate that the peptides have efficacy for preventing and treating malaria.

Methods

Preparation of *Plasmodium* Sporozoites:

3-5 day-old *Anopheles stephensi* mosquitoes were fed on anesthetized *P. berghei* (NK65)-infected Swiss Webster mice which had been checked by blood smear for the abundance of gametocyte-stage parasites. Salivary gland sporozoites were harvested on days 18 to 21 post-infective blood meal. The mosquitoes were rinsed in 70% ethanol and washed in Dulbecco's Modified Eagle Medium (DMEM) before salivary gland dissection. The glands were gently ground, spun at 80×g for 3 min to remove mosquito debris and sporozoites counted in a hemocytometer.

Sporozoite Development Assay:

Hepa 1-6 cells (ATCC CRL-1830, American Type Culture Collection, Manassas, Va.), a mouse hepatoma cell line permissive for *P. berghei* sporozoite development were seeded ($8\times10^4$ cells/well) in Lab-Tek permanox chamber slides (Nalgene Nunc Corp., Naperville, Ill.) and grown until confluent. On the day of the experiment, sporozoites were dissected from mosquitoes and pre-incubated with Dulbecco's Modified Eagle Medium (DMEM; Invitrogen, Carlsbad, Calif.) with 1% BSA alone or with the indicated polypeptide at 50 μg/ml for 1 hr at 28° C. and plated on cells in the continued presence of the inhibitor in DMEM containing 10% fetal calf serum (complete medium). After 1 hr at 37° C., the medium containing unattached sporozoites and polypeptide was removed and replaced with complete medium. 40 hours later the cells were fixed with cold methanol and exoerythrocytic stages (EEFs) were stained with mAb 2E6 (Tsuji, M., D. Mattei, R. S. Nussenzweig, D. Eichinger, and F. Zavala. 1994. Demonstration of heat-shock protein 70 in the sporozoite stage of malaria parasites. *Parasitology Research* 80:16-21.) followed by anti-mouse immunoglobulin conjugated to FITC. The number of EEFs in each well were counted with a 40× objective on a Nikon fluorescent microscope. In other experiments, Hepa1-6 cells were pretreated with the polypeptides at 50 μg/ml in complete medium for 1 hour, washed and then sporozoites were added in complete medium without polypeptide and the assay was continued as outlined above.

Results

FIG. 5 shows that both MU10 and MU4 inhibit entry of *P. berghei* into Hep 1-6 cells. In additional experiments in which cells were treated with these peptides, washed using cell culture media, before final challenge with *P. berghei*, MU4 retained its ability to block *P. berghei* entry, suggesting that this compound may bind the surface of these cells irreversibly, with this then later preventing entry of the parasite. This rodent model is widely used to study the entry of *Plasmodium* into liver; activity as demonstrated here almost certainly means that entry of *Plasmodium falciparum* (and other *Plasmodium* species) into liver would be similarly prevented.

These data illustrate that peptides according to the invention may be used in the treatment of malaria and other protist infections.

The invention claimed is:

1. A method of reducing the likelihood of, or treating a fungal or protist contamination of a non-living object or surface required to be aseptic against fungal or protist contamination, comprising:

applying to the object or surface an amount of a 14-29 amino acid polypeptide that is effective for killing or inhibiting growth of fungi or protists;

wherein the polypeptide is derived from a Heparan Sulphate Proteoglycan (HSPG) receptor binding region of an apolipoprotein and comprises at least two RKR motifs.

2. The method according to claim 1 wherein the polypeptide is derived from a Heparan Sulphate Proteoglycan (HSPG) receptor binding region of apolipoprotein B or apolipoprotein E.

3. The method according to claim 1 wherein the polypeptide is derived from a Heparan Sulphate Proteoglycan (HSPG) receptor binding region of apolipoprotein B LDL receptor binding domain cluster B or apolipoprotein E LDL receptor binding domain cluster B.

4. The method according to claim 1 wherein the polypeptide comprises a tandem dimer repeat of SEQ ID NO: 5; SEQ ID NO: 6; or SEQ ID NO: 7; or a tandem dimer repeat of SEQ ID NO: 5; SEQ ID NO: 6; or SEQ ID NO: 7 wherein at least one amino acid, other than RKR motifs, is replaced by an Arginine (R), Tyrosine (Y), Methionine (M), Isoleucine (I), Phenylalanine (F), Tryptophan (W), Cysteine (C).

5. The method according to claim 1 wherein at least one amino acid, other than RKR motifs, is replaced by an Arginine (R), Phenylalanine (F) or Tryptophan (W).

6. The method according to claim 1 wherein the polypeptide is of formula (I):

abcRKRxyza'b'c'RKRx'y'z' (I)

wherein a & a'=is independently selected from Arginine (R): Tyrosine (Y); Methionine (M); Isoleucine (I); Phenylalanine (F); Tryptophan (W); Leucine (L); Lysine (K); Histidine (H); Cysteine (C) or is deleted, b & b'=is independently selected from Arginine (R): Tyrosine (Y); Methionine (M); Isoleucine (I); Phenylalanine (F); Tryptophan (W); Leucine (L); Lysine (K); Cysteine (C) or is deleted, c & c'=is independently selected from Arginine (R): Tyrosine (Y); Methionine (M); Isoleucine (I); Phenylalanine (F); Tryptophan (W); Leucine (L); Lysine (K); Histidine (H); Threonine (T); Cysteine (C); or is deleted, x & x'=is independently selected from either Arginine (R): Tyrosine (Y); Methionine (M); Isoleucine (I); Phenylalanine (F); Tryptophan (W); Leucine (L); Lysine (K); Histidine (H); Glycine (G); Cysteine (C) or is deleted, y & y'=is independently selected from Arginine (R): Tyrosine (Y); Methionine (M); Isoleucine (I); Phenylalanine (F); Tryptophan (W); Leucine (L); Lysine (K); Histidine (H); Cysteine (C) or is deleted, z & z'=is independently selected from Arginine (R): Tyrosine (Y); Methionine (M); Isoleucine (I); Phenylalanine (F); Tryptophan (W); Leucine (L); Lysine (K); Histidine (H); Cysteine (C) or is deleted, wherein the polypeptide is 14-18 amino acids in length; and wherein optionally an amino acid that is independently selected from Arginine (R): Tyrosine (Y); Methionine (M); Isoleucine (I); Phenylalanine (F); Tryptophan (W); Leucine (L); Lysine (K) and Histidine (H) may be added before the amino acid at position "a".

7. The method according to claim 1 wherein the polypeptide comprises a repeat of $apoE_{141-149}$ (SEQ ID NO: 5) wherein at least one amino acid, other than RKR motifs, is replaced by an Arginine (R), Tyrosine (Y), Methionine (M), Isoleucine (I), Phenylalanine (F), Tryptophan (W), Cysteine (C).

8. The method according to claim 7 wherein the polypeptide comprises at least two substitutions independently selected from Tryptophan (W); Arginine (R); Lysine (K); Tyrosine (Y) or Phenylalanine (F) substitutions.

9. The method according to claim 7 wherein the polypeptide comprises the amino acid sequences as defined by any one of SEQ ID NOs: 8-34.

10. The method according to claim 1 wherein the polypeptide comprises a repeat of $apoB_{3359-3367}$ (SEQ ID NO: 6).

11. The method according to claim 10 wherein the polypeptide comprises the amino acid sequences as defined by any one of SEQ ID NOs. 36-55.

12. The method according to claim 1 for reducing the likelihood, or treating an Ascomycete contamination.

13. The method according to claim 1 for reducing the likelihood, or treating a contamination with a fungus independently selected from the group consisting of *Aspergillus* spp.; *Candida* spp,; and *Fusarium* spp.

14. The method according to claim 1 for reducing the likelihood, or treating a Sarcodina contamination.

15. The method according to claim 1 for reducing the likelihood, or treating a *Plasmodium* spp or *Acanthamoeba* contamination.

16. The method according to claim 1, wherein the polypeptide is applied to an object selected from: medical devices, lenses, contact lenses, catheters, stents, wound healing dressings, contraceptives, surgical implants and replacement joints.

17. The method according to claim 1, wherein the polypeptide is applied to a surface selected from: hospital ward surfaces, operating theatre surfaces, kitchen surfaces, sanitary surfaces.

18. The method according to claim 1, wherein the polypeptide is applied to a contact lens.

* * * * *